US008309078B2

United States Patent
Percudani et al.

(10) Patent No.: US 8,309,078 B2
(45) Date of Patent: Nov. 13, 2012

(54) METHOD FOR CONVERSION OF URIC ACID TO ALLANTOIN AND RELATED ENZYMES

(75) Inventors: Riccardo Percudani, Parma (IT); Claudia Folli, Parma (IT); Ileana Ramazzina, Mantova (IT)

(73) Assignee: Università degli Studi di Parma, Parma (IT)

( * ) Notice: Subject to any disclaimer, the term of this patent is extended or adjusted under 35 U.S.C. 154(b) by 917 days.

(21) Appl. No.: 12/092,706

(22) PCT Filed: Nov. 7, 2006

(86) PCT No.: PCT/IT2006/000778
§ 371 (c)(1),
(2), (4) Date: Oct. 6, 2008

(87) PCT Pub. No.: WO2007/052326
PCT Pub. Date: May 10, 2007

(65) Prior Publication Data
US 2009/0280101 A1 Nov. 12, 2009

Related U.S. Application Data

(60) Provisional application No. 60/734,327, filed on Nov. 7, 2005.

(51) Int. Cl.
*C12N 9/88* (2006.01)
*A61K 38/51* (2006.01)
*C12P 17/10* (2006.01)

(52) U.S. Cl. .................. 424/94.5; 435/232; 435/121

(58) Field of Classification Search ................ None
See application file for complete search history.

(56) References Cited

FOREIGN PATENT DOCUMENTS
WO   2004/072267   *   8/2004

OTHER PUBLICATIONS

Y. Lee et al. "Transthyretin-Related Proteins Function to Facilitate the Hydrolysis of 5-Hydroxyisourate, The End Product of the Uricase Reaction", FEBS Letters 579: 4769-4774. (Aug. 2005).*
GenBank Accession No. XP_696168 (Jun. 2005).*
GenBank Accession No. NP_001072641 (Mar. 2011).*
UniProt Accesion No. A6NGE7 (Jan. 2008).*

* cited by examiner

*Primary Examiner* — Rebecca E. Prouty
(74) *Attorney, Agent, or Firm* — Lucas & Mercanti, LLP

(57) ABSTRACT

A polypeptide molecule able to selectively modulate uric acid conversion into S(+)- allantoin is described. A pharmaceutical composition for treating uric acid related disorders and a process to selectively modulate uric acid conversion into S(+)-allantoin are also disclosed.

5 Claims, 7 Drawing Sheets

Fig. 5

| OHCU decarboxylase (COG3195) | |
|---|---|
| | `          1         10         20         30         40` |
| Mus_musculus | `........MDMVK.VNSMDFGEFVDVFGNIVEKCPLIAAAVWS...QRPFSG.LEDLEN` |
| Canis_familiaris | `........MDIEK.VNSMDFGEFVDVFGNVIERCPLIAAAVWS...QRPFSN.LEDLEK` |
| Xenopus_ | `........MDLNT.INSMSYEEFLDIFGNIIERCPIITAAIWS...QFPFAS.VTELEN` |
| Takifugu_rubipes | `........MDIRA.VNDLSFEEFVNIFGNLVEKCPIVAATVWS...ERPFGS.FTALEK` |
| Danio_rerio | `........MDINV.VNALAYEDFVKLFGNVVEKCPLISAAIWS...YRPFKD.LADIEA` |
| Strongylocentrotus | `.....MAEKFTIEA.INQQEYEEFIENFEILDEHGILIAGAVWS...HRPFQS.FDHLHR` |
| Candida_albicans | `........MALPTIESFKRLSSKDKRQVLDHLFEPCNTLSNFIFIKVLHQQYNTYPEFINL` |
| Gibberella_zeae | `......MTLLPPKE.LRIANETEQIKTLDLLFEPSPAIHSTLIPVLRESEYTSYPELIDA` |
| Arabidopsis_thaliana | `..............MAM...EIGEDEWKVCCGS.SEFAKQMST...SGPLTS.QEAIYT` |
| Oryza_sativa | `...............MATTRGQLPVEDVLRVNGS.RRFAAALAA...ASPFASLADALLA` |
| Streptomyces_avermitilis | `..MTSTSTPPGLAR.FNDLGEHAALAALHEACAS.TTWARRLIA...ARPYAT.ADDLYT` |
| Nocardia_farcinica | `...MTHPAPAGIAA.FDALPAAAATAALLEVCAS.PEWARRVVA...GRPYGT.AERLYA` |
| Bacillus_halodurans | `MMGMAVSTKLSIDE.VNMLEKEDFVTKIGPIFEHSPWVAERAWA...HRPFTS.AENMYE` |
| Deinococcus_radiodurans | `....MTRTPLTLEQ.LNALSDDAFTEHFAGVLEHSPHYARRAAA...GRPEAD.VEEVAA` |

| | |
|---|---|
| | `           50                 60         70         80         90` |
| Mus_musculus | `HFFAFIDAL............PRSGQEGILRCHDLAGRDLQQGTLTA.ESQREQSQAG` |
| Canis_familiaris | `HFFDFIDAL............PQSGREGILRCHDLAGRELQQGTLSA.ESRREQSGAG` |
| Xenopus_ | `SVYDFIESL............PLTGKEGILRCHDLAGRDLMRGTLTD.ESQTEQAQAG` |
| Takifugu_rubipes | `AIHDFIDHL............PQSGKEGLLRCHDLAGRDLQRGTLTQ.ESRVEQVAAG` |
| Danio_rerio | `RISEFIHSL............PDSGKEGILRCHDLAGRDLQSGTLTP.ESQEQSQAG` |
| Strongylocentrotus | `CFCDFMDSL............PESGKQSILRCHNLAGKLARQGKLTS.ESEQEQASAG` |
| Candida_albicans | `VRKELLEFLKQSETFQSQYQGEINPVINEIISAHRLGEPKKETLS......VHSNNEQK` |
| Gibberella_zeae | `CRSRLVSLASSS......SPTNPDATLLSILGSHRLGAKKVESA..........QSAA` |
| Arabidopsis_thaliana | `ARDIWFNQV............NVTDWLEATSAHQIGNTPSPSINSDFARRSVSEQSTA` |
| Oryza_sativa | `ARRIWLNEV............DVNGWLEAFAAHAIGTTSSSAP.....KWCKEEQSAA` |
| Streptomyces_avermitilis | `ASDAAMAEL............TAADLAQAMAGHPIGRP..KPG.....DPTSAREQRG` |
| Nocardia_farcinica | `AAERVLADL............PEREIDRALAGHRIGE...QPG.....GAAASHEQAG` |
| Bacillus_halodurans | `CMLEKVYEA............DKRLQLALLRAHDLG....TRLEISE.TSQSEQQRAG` |
| Deinococcus_radiodurans | `AFARAVAAD............EPGAQVQLIRAHDLAGKAALAGELTA.ESASEQTSAG` |

| | |
|---|---|
| | `           100        110        120        130        140` |
| Mus_musculus | `LTSLDTDDRLRLQQLNAQVRERHG.FPPVLAARLSDR.ATVPRELARRLQCQPES.ELRT` |
| Canis_familiaris | `LASLDADERLRLAELNAQVRARHG.FPPVLAARRSHR.AAVPRELARLRCPPAQ.ELRT` |
| Xenopus_ | `LTALTPKERETLNLLNSQVKAKHG.FPPVICAKMSDK.NKIMRELASRLQNEQSQ.ELQI` |
| Takifugu_rubipes | `LDALGSEEASRMERLNDEVKQRHG.FPPVICARMNDK.ATILHQMTERCQNEPAL.ETLR` |
| Danio_rerio | `MTTLDSAEIVHMYRLNSEVKERHG.FPPVICARLNNK.ADIVRQLSELKNHRTA.ERER` |
| Strongylocentrotus | `LSSLTDEQYNEIHKNNDIVRKKHS.FPPVICARENKI.AAILQGLQTRIQNAREL.ELQK` |
| Candida_albicans | `TLNNDPEIIKKLKELNAAVEKTHPGLRYVVFVNGRSRH.EIMDNMQKRIERNDINLERV.` |
| Gibberella_zeae | `EQANLQGQGEELAKLNQEVEEKHPGLRYVVFVNGRGRP.EIMENMKARISRGVFSKE.VA` |
| Arabidopsis_thaliana | `FATTSASALQEEAWNVLNKKHG.FIFICASGRTH.AEMLHALKERYENRPIV.ELEI` |
| Oryza_sativa | `LATATDSTAQELADWNARVREKHG.FVFMICASGRTA.PEVLAELKRRYENRPIV.LEI` |
| Streptomyces_avermitilis | `MAGASEELKADMLELNLAVQEKHG.HVFLICATGRTG.EQMRDAVRERIGNAPER.EREI` |
| Nocardia_farcinica | `VAGADAATRAALAAGNRAVERRHG.RIYLVSAAGRSA.DELLAILEARLRNDPEV.ETRV` |
| Bacillus_halodurans | `LSQLTEEEFAVFAELNKCVDTHR.FPFIMAVRGQTKN.SIKEQMRKLVNDEEQ.ERKT` |
| Deinococcus_radiodurans | `LDRLSPEEYAEFQRLNAAMHERHG.LPYVVCVRENTKD.TIFEGARRLTHTQEE.EQAA` |

| | |
|---|---|
| | `           150        160        170` |
| Mus_musculus | `.ALGEVKKISHLR.LTDLLGAHSHSARVELP.......` |
| Canis_familiaris | `.ALAEVKKIGHLR.LADLLGTP..PARL..........` |
| Xenopus_ | `.GIAEVKKICHLR.VNDLFLNVKLPTKL..........` |
| Takifugu_rubipes | `.GIEEVKKISSLR.LHSIILVDTPRL............` |
| Danio_rerio | `.AIEEVKKICSLR.LHNIVLSDIQTKL...........` |
| Strongylocentrotus | `.GIEEVKKISYYR.LLDMIQEKTLSPKKPKL.......` |
| Candida_albicans | `EAFNAMCDIALDRANKLGTKL.................` |
| Gibberella_zeae | `EALQAMCDIAKDRASKLDAKL.................` |
| Arabidopsis_thaliana | `.AAMEQMKITELR.MAKLFSDKAKVISETDSSSPVST` |
| Oryza_sativa | `.AAQEELKITELR.LAKLFASEPVAPPSSTVGGPTSQS` |
| Streptomyces_avermitilis | `.VRTELGKINRIR.LARLVEEDAHA.............` |
| Nocardia_farcinica | `.LREELAKINRLR.LGRLPAVTGEDPV...........` |
| Bacillus_halodurans | `.ALREVAKIAKFR.LADLVVMGSRS.............` |
| Deinococcus_radiodurans | `.ALHEIGRIARLR.ILDLVQEGRQEKRMDGRLIRIP..` |

Fig. 7

SEQUENCE LISTING

```
<160> NUMBER OF SEQ ID NOS: 39

<210> SEQ ID NO 1
<211> LENGTH: 357
<212> TYPE: DNA
<213> ORGANISM: Mus musculus
<220> FEATURE:
<221> NAME/KEY: CDS
<222> LOCATION: (1)..(354)
```

-continued

<400> SEQUENCE: 1

```
atg gct acc gag agc agt ccc ctg act act cac gtt cta gac act gcc        48
Met Ala Thr Glu Ser Ser Pro Leu Thr Thr His Val Leu Asp Thr Ala
1               5                   10                  15 tca ggg ctc cct gcc caa ggc ctc tgc ctc cgg ctg tcc cgc ctg gag        96
Ser Gly Leu Pro Ala Gln Gly Leu Cys Leu Arg Leu Ser Arg Leu Glu
            20                  25                  30 gcc ccc tgc cag cag tgg atg gag ctg agg aca agc tac aca aac ctg       144
Ala Pro Cys Gln Gln Trp Met Glu Leu Arg Thr Ser Tyr Thr Asn Leu
        35                  40                  45 gac ggt cgc tgt cct ggg ctc ctg aca cca agc cag ata aag cca ggc       192
Asp Gly Arg Cys Pro Gly Leu Leu Thr Pro Ser Gln Ile Lys Pro Gly
    50                  55                  60 acc tat aag ctg ttc ttc gac aca gag cgc tac tgg aaa gag cgg ggt       240
Thr Tyr Lys Leu Phe Phe Asp Thr Glu Arg Tyr Trp Lys Glu Arg Gly
65                  70                  75                  80 caa gag agc ttt tac ccc tat gta gag gtg gtt ttc act att aca aag       288
Gln Glu Ser Phe Tyr Pro Tyr Val Glu Val Val Phe Thr Ile Thr Lys
                85                  90                  95 gag acc cag aag ttc cac gta cct ctg ctg ctg agc cca tgg tcc tac       336
Glu Thr Gln Lys Phe His Val Pro Leu Leu Leu Ser Pro Trp Ser Tyr
            100                 105                 110 acc acc tac cgg ggg agt taa                                           357
Thr Thr Tyr Arg Gly Ser
        115
```

<210> SEQ ID NO 2
<211> LENGTH: 118
<212> TYPE: PRT
<213> ORGANISM: Mus musculus

<400> SEQUENCE: 2

```
Met Ala Thr Glu Ser Ser Pro Leu Thr Thr His Val Leu Asp Thr Ala
1               5                   10                  15

Ser Gly Leu Pro Ala Gln Gly Leu Cys Leu Arg Leu Ser Arg Leu Glu
            20                  25                  30

Ala Pro Cys Gln Gln Trp Met Glu Leu Arg Thr Ser Tyr Thr Asn Leu
        35                  40                  45

Asp Gly Arg Cys Pro Gly Leu Leu Thr Pro Ser Gln Ile Lys Pro Gly
    50                  55                  60

Thr Tyr Lys Leu Phe Phe Asp Thr Glu Arg Tyr Trp Lys Glu Arg Gly
65                  70                  75                  80

Gln Glu Ser Phe Tyr Pro Tyr Val Glu Val Val Phe Thr Ile Thr Lys
                85                  90                  95

Glu Thr Gln Lys Phe His Val Pro Leu Leu Leu Ser Pro Trp Ser Tyr
            100                 105                 110

Thr Thr Tyr Arg Gly Ser
        115
```

<210> SEQ ID NO 3
<211> LENGTH: 537
<212> TYPE: DNA
<213> ORGANISM: Mus musculus
<220> FEATURE:
<221> NAME/KEY: CDS
<222> LOCATION: (1)..(534)

<400> SEQUENCE: 3

```
atg gac atg gtg aag gtc aat tcc atg gac ttc gga gaa ttt gtg gat        48
Met Asp Met Val Lys Val Asn Ser Met Asp Phe Gly Glu Phe Val Asp
1               5                   10                  15
```

| | | | | | | | | | | | | | | | | |
|---|---|---|---|---|---|---|---|---|---|---|---|---|---|---|---|---|
| gtg | ttt | ggg | aac | att | gtt | gag | aaa | tgc | cct | ctg | att | gcc | gct | gct | gtc | 96 |
| Val | Phe | Gly | Asn | Ile | Val | Glu | Lys | Cys | Pro | Leu | Ile | Ala | Ala | Ala | Val | |
| | | | 20 | | | | 25 | | | | 30 | | | | | |
| tgg | tcc | cag | cgt | cca | ttc | tct | ggc | ttg | gaa | gac | tta | gaa | aat | cac | ttt | 144 |
| Trp | Ser | Gln | Arg | Pro | Phe | Ser | Gly | Leu | Glu | Asp | Leu | Glu | Asn | His | Phe | |
| | | 35 | | | | 40 | | | | 45 | | | | | | |
| ttt | gcc | ttt | att | gat | gct | ctc | ccg | aga | tca | ggc | cag | gaa | ggc | atc | ctg | 192 |
| Phe | Ala | Phe | Ile | Asp | Ala | Leu | Pro | Arg | Ser | Gly | Gln | Glu | Gly | Ile | Leu | |
| 50 | | | | | 55 | | | | | 60 | | | | | | |
| cgt | tgt | cac | ccg | gac | cta | gct | ggc | cgt | gat | ctg | caa | cag | ggc | aca | ctc | 240 |
| Arg | Cys | His | Pro | Asp | Leu | Ala | Gly | Arg | Asp | Leu | Gln | Gln | Gly | Thr | Leu | |
| 65 | | | | 70 | | | | | 75 | | | | | 80 | | |
| act | gct | gag | tca | cag | cgt | gag | cag | agc | caa | gca | ggt | ctc | act | agc | cta | 288 |
| Thr | Ala | Glu | Ser | Gln | Arg | Glu | Gln | Ser | Gln | Ala | Gly | Leu | Thr | Ser | Leu | |
| | | | | 85 | | | | 90 | | | | | 95 | | | |
| gac | acc | gac | gac | agg | ctg | cgg | ctg | caa | caa | ctc | aat | gct | cag | tac | cgt | 336 |
| Asp | Thr | Asp | Asp | Arg | Leu | Arg | Leu | Gln | Gln | Leu | Asn | Ala | Gln | Tyr | Arg | |
| | | | 100 | | | | | 105 | | | | 110 | | | | |
| gag | cgc | ttc | ggc | ttt | ccg | ttc | gtt | ctg | gca | gcg | cgc | ctg | agc | gac | cgt | 384 |
| Glu | Arg | Phe | Gly | Phe | Pro | Phe | Val | Leu | Ala | Ala | Arg | Leu | Ser | Asp | Arg | |
| | | 115 | | | | | 120 | | | | 125 | | | | | |
| gcc | act | gtg | ccc | cga | gag | cta | gcc | cgc | agg | ctt | cag | tgc | cag | ccg | gaa | 432 |
| Ala | Thr | Val | Pro | Arg | Glu | Leu | Ala | Arg | Arg | Leu | Gln | Cys | Gln | Pro | Glu | |
| | 130 | | | | | 135 | | | | 140 | | | | | | |
| tcc | gag | ctg | cgc | acc | gcc | ctg | ggt | gaa | gtg | aag | aag | atc | agc | cac | ctg | 480 |
| Ser | Glu | Leu | Arg | Thr | Ala | Leu | Gly | Glu | Val | Lys | Lys | Ile | Ser | His | Leu | |
| 145 | | | | | 150 | | | | | 155 | | | | | 160 | |
| cgc | ctg | aca | gat | ttg | ctc | ggt | gcc | cac | tcc | cac | tcc | gcc | agg | gtg | gaa | 528 |
| Arg | Leu | Thr | Asp | Leu | Leu | Gly | Ala | His | Ser | His | Ser | Ala | Arg | Val | Glu | |
| | | | | 165 | | | | 170 | | | | | 175 | | | |
| cta | ccg | tga | | | | | | | | | | | | | | 537 |
| Leu | Pro | | | | | | | | | | | | | | | |

<210> SEQ ID NO 4
<211> LENGTH: 178
<212> TYPE: PRT
<213> ORGANISM: Mus musculus

<400> SEQUENCE: 4

Met Asp Met Val Lys Val Asn Ser Met Asp Phe Gly Glu Phe Val Asp
1               5                   10                  15

Val Phe Gly Asn Ile Val Glu Lys Cys Pro Leu Ile Ala Ala Ala Val
                20                  25                  30

Trp Ser Gln Arg Pro Phe Ser Gly Leu Glu Asp Leu Glu Asn His Phe
            35                  40                  45

Phe Ala Phe Ile Asp Ala Leu Pro Arg Ser Gly Gln Glu Gly Ile Leu
    50                  55                  60

Arg Cys His Pro Asp Leu Ala Gly Arg Asp Leu Gln Gln Gly Thr Leu
65                  70                  75                  80

Thr Ala Glu Ser Gln Arg Glu Gln Ser Gln Ala Gly Leu Thr Ser Leu
                85                  90                  95

Asp Thr Asp Asp Arg Leu Arg Leu Gln Gln Leu Asn Ala Gln Tyr Arg
            100                 105                 110

Glu Arg Phe Gly Phe Pro Phe Val Leu Ala Ala Arg Leu Ser Asp Arg
        115                 120                 125

Ala Thr Val Pro Arg Glu Leu Ala Arg Arg Leu Gln Cys Gln Pro Glu
    130                 135                 140

Ser Glu Leu Arg Thr Ala Leu Gly Glu Val Lys Lys Ile Ser His Leu 145             150             155             160
Arg Leu Thr Asp Leu Leu Gly Ala His Ser His Ser Ala Arg Val Glu
                165             170             175

Leu Pro

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      Mura H upstream primer

<400> SEQUENCE: 5
catatggcta ccgagagcag tc                                          22

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      Mura H downstream primer

<400> SEQUENCE: 6
ggatcccttt aactcccccg g                                           21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      Mura D upstream primer

<400> SEQUENCE: 7
catatggaca tggtgaaggt caat                                        24

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      Mura D downstream primer

<400> SEQUENCE: 8
ggatcctcac ggtagttcca c                                           21

<210> SEQ ID NO 9
<211> LENGTH: 141
<212> TYPE: PRT
<213> ORGANISM: Mus musculus

<400> SEQUENCE: 9

Met Ser Ser Arg Thr Ala Pro Arg Leu Met Thr Leu Gln Arg His Leu
1               5                   10                  15

Gly Trp Pro Gln Ala Gly Asn Met Ala Thr Glu Ser Ser Pro Leu Thr
            20                  25                  30

Thr His Val Leu Asp Thr Ala Ser Gly Leu Pro Ala Gln Gly Leu Cys
        35                  40                  45

Leu Arg Leu Ser Arg Leu Glu Ala Pro Cys Gln Gln Trp Met Glu Leu
    50                  55                  60

Arg Thr Ser Tyr Thr Asn Leu Asp Gly Arg Cys Pro Gly Leu Leu Thr

```
                65                  70                  75                  80
Pro Ser Gln Ile Lys Pro Gly Thr Tyr Lys Leu Phe Phe Asp Thr Glu
                85                  90                  95

Arg Tyr Trp Lys Glu Arg Gly Gln Glu Ser Phe Tyr Pro Tyr Val Glu
                100                 105                 110

Val Val Phe Thr Ile Thr Lys Glu Thr Gln Lys Phe His Val Pro Leu
                115                 120                 125

Leu Leu Ser Pro Trp Ser Tyr Thr Thr Tyr Arg Gly Ser
                130                 135                 140

<210> SEQ ID NO 10
<211> LENGTH: 141
<212> TYPE: PRT
<213> ORGANISM: Canis familiaris

<400> SEQUENCE: 10

Met Ser Ser Gly Ala Ala Pro Arg Leu Arg Ala Leu Gln Arg His Leu
1               5                   10                  15

Gly Ser Ser Gln Gly Gly Gly Met Glu Gln Ile Ser Ser Pro Leu Thr
                20                  25                  30

Thr His Val Leu Asp Thr Ala Ser Gly Leu Pro Ala Gln Gly Leu Cys
                35                  40                  45

Leu Arg Leu Ser Arg Leu Glu Asp His Gly Gln Gln Trp Thr Glu Leu
    50                  55                  60

Lys Lys Ser Tyr Thr Asp Ser Asp Gly Arg Cys Pro Gly Leu Leu Pro
65              70                  75                  80

Pro Gly Pro Met Lys Ala Gly Thr Tyr Lys Leu Ser Phe Asp Thr Glu
                85                  90                  95

Gly Tyr Trp Lys Lys Lys Gly Gln Glu Ser Phe Tyr Pro Tyr Val Glu
                100                 105                 110

Val Val Phe Thr Ile Ala Asn Glu Thr His Arg Phe His Val Pro Leu
                115                 120                 125

Leu Leu Ser Pro Trp Ser Tyr Thr Thr Tyr Arg Gly Ser
                130                 135                 140

<210> SEQ ID NO 11
<211> LENGTH: 141
<212> TYPE: PRT
<213> ORGANISM: Xenopus tropicalis

<400> SEQUENCE: 11

Met Ser Arg Gly Arg Leu Gln Leu Ile Gln Gln His Leu His Gly Thr
1               5                   10                  15

Pro Ala Arg Glu Gln Gly Met Ser Ala Ala Ser Val Ser Gln Leu Thr
                20                  25                  30

Thr His Val Leu Asn Val Ser Glu Gly Ile Pro Ala Lys Gly Leu Thr
                35                  40                  45

Leu Ser Leu Ser Arg His Asp Val Ser Gln Gly Lys Trp Leu Gln Leu
    50                  55                  60

Ser Arg Ser Val Thr Asn Glu Asp Gly Arg Cys Pro Gly Leu Leu Arg
65              70                  75                  80

Gly Glu Gly Leu Cys Ala Gly Thr Tyr Gln Leu Arg Phe Asp Thr Gly
                85                  90                  95

Asp Tyr Trp Lys Gln Met His Lys Glu Ser Phe Tyr Pro Tyr Val Glu
                100                 105                 110

Ile Val Phe Thr Ile Thr Asp Gln Lys Gln Lys Tyr His Val Pro Leu
                115                 120                 125
```

```
Leu Leu Ser Pro Phe Ser Tyr Thr Thr Tyr Arg Gly Ser
    130                 135                 140
```

<210> SEQ ID NO 12
<211> LENGTH: 139
<212> TYPE: PRT
<213> ORGANISM: Tetraodon nigroviridis

<400> SEQUENCE: 12

```
Met Ser Ala His Arg Leu Gln Leu Leu Lys Gly His Leu Glu Ala Glu
1               5                   10                  15

Asn Lys Ile Ala Ala Met Ala Gly Ser Pro Ser Pro Leu Thr Thr His
            20                  25                  30

Val Leu Asn Thr Gly Met Gly Ile Pro Ala Ser Asn Met Ala Leu Asn
        35                  40                  45

Leu Tyr Arg Lys Asp Pro Ser Asn Asp Thr Trp Ser Leu Leu Lys Thr
    50                  55                  60

Gly Thr Thr Asn Glu Asp Gly Arg Cys Pro Gly Leu Ile Thr Ser Gln
65                  70                  75                  80

Met Phe Thr Ser Gly Val Tyr Lys Ile His Phe Asp Thr Ala Gln Tyr
                85                  90                  95

Trp Glu Ser Met Gly Gln Thr Ser Phe Tyr Pro Tyr Val Glu Ile Val
                100                 105                 110

Phe Ile Ile Asn Asp Pro Gly Gln Lys Tyr His Ile Pro Leu Leu Leu
            115                 120                 125

Ser Arg Phe Ser Tyr Thr Thr Tyr Arg Gly Ser
    130                 135
```

<210> SEQ ID NO 13
<211> LENGTH: 139
<212> TYPE: PRT
<213> ORGANISM: Takifugu rubripes

<400> SEQUENCE: 13

```
Met Ser Ala Gln Arg Leu Gln Leu Leu Lys Gly His Ile Leu Pro Glu
1               5                   10                  15

Asn Lys Thr Thr Ala Met Ala Gly Ser Pro Gly Pro Leu Thr Thr His
            20                  25                  30

Val Leu Asn Thr Ala Met Gly Ile Pro Ala Ser Asn Leu Ala Leu His
        35                  40                  45

Leu Tyr Arg Gln Asp Pro Ser Thr Asn Ala Trp Ser Leu Ile Lys Thr
    50                  55                  60

Gly Thr Thr Asn Glu Asp Gly Arg Cys Pro Gly Leu Ile Thr Pro Gln
65                  70                  75                  80

Ala Phe Thr Ser Asp Val Tyr Lys Ile His Phe Glu Thr Ala Lys Tyr
                85                  90                  95

Trp Glu Arg Ile Gly Glu Thr Gly Phe Tyr Pro Tyr Val Glu Ile Val
                100                 105                 110

Phe Thr Ile Asn Asp Pro Gly Gln Lys Tyr His Ile Pro Leu Leu Leu
            115                 120                 125

Ser Pro Phe Ser Tyr Ser Thr Tyr Arg Gly Ser
    130                 135
```

<210> SEQ ID NO 14
<211> LENGTH: 138
<212> TYPE: PRT
<213> ORGANISM: Danio rerio

```
<400> SEQUENCE: 14

Met Asn Arg Leu Gln His Ile Arg Gly His Ile Val Ser Ala Asp Lys
1               5                   10                  15

His Ile Asn Met Ser Ala Thr Leu Pro Ser Pro Leu Ser Thr His Val
            20                  25                  30

Leu Asn Ile Ala Gln Gly Val Pro Gly Ala Asn Met Thr Ile Val Leu
        35                  40                  45

His Arg Leu Asp Pro Val Ser Ser Ala Trp Asn Ile Leu Thr Thr Gly
    50                  55                  60

Ile Thr Asn Asp Asp Gly Arg Cys Pro Gly Leu Ile Thr Lys Glu Asn
65                  70                  75                  80

Phe Ile Ala Gly Val Tyr Lys Met Arg Phe Glu Thr Gly Lys Tyr Trp
                85                  90                  95

Asp Ala Leu Gly Glu Thr Cys Phe Tyr Pro Tyr Val Glu Ile Val Phe
            100                 105                 110

Thr Ile Thr Asn Thr Ser Gln His Tyr His Val Pro Leu Leu Leu Ser
        115                 120                 125

Arg Phe Ser Tyr Ser Thr Tyr Arg Gly Ser
    130                 135

<210> SEQ ID NO 15
<211> LENGTH: 147
<212> TYPE: PRT
<213> ORGANISM: Strongylocentrotus purpuratus

<400> SEQUENCE: 15

Met Gly Ser Cys Lys Arg Val Glu Ala Leu Asn Ser His Leu Ser Ala
1               5                   10                  15

Pro Ala Asp Glu Gly Asn Val Ala Leu Thr Thr Val Glu Thr Ala Gly
            20                  25                  30

Gly Lys Pro Asn Ser Pro Leu Thr Ser His Val Leu Asp Thr Ala Arg
        35                  40                  45

Gly Ser Pro Ala Ala Asn Leu Arg Ile Glu Val Tyr His Leu Met Ala
    50                  55                  60

Gly Gln Trp Lys Lys Ile Ser Glu Gly Gln Thr Asn Ser Asp Gly Arg
65                  70                  75                  80

Cys Pro Gly Leu Leu Thr Met Gly Gln Phe Ile Pro Gly Ile Tyr Lys
                85                  90                  95

Ile Leu Phe Asp Thr Gly Ser Tyr Phe Lys Ala Asn Asn Ile Lys Gly
            100                 105                 110

Phe Tyr Pro Phe Val Glu Ile Val Phe Glu Ile Glu Asp Val Asn Gln
        115                 120                 125

His Tyr His Val Pro Leu Leu Leu Ser Pro Phe Ser Tyr Ser Thr Tyr
    130                 135                 140

Arg Gly Ser
145

<210> SEQ ID NO 16
<211> LENGTH: 162
<212> TYPE: PRT
<213> ORGANISM: Candida albicans

<400> SEQUENCE: 16

Met Ser Val Asp Pro Ile Thr Cys His Ile Leu Asp Thr Thr Leu Gly
1               5                   10                  15

Thr Pro Ala Ser Gly Val Ile Val Gln Leu Phe His Ile Ser Asn Asp
            20                  25                  30
```

```
Pro Leu Leu Ser Ser Ile Ser Glu Asp Thr Thr Thr Asn Gly Lys
            35                  40                  45

His Phe Ala Met Ala Lys Thr Asp Asn Asp Gly Arg Ile Lys Gln Trp
 50                  55                  60

Ile Ile Asn Pro Asn Gly Asp Phe Gln Asn Leu Gly Ile Thr Lys Asn
 65                  70                  75                  80

Ser Ser Lys Asn Asn His Gln Ser Trp Asn Asn Leu Lys Pro Gly Ile
                 85                  90                  95

Tyr Lys Ala Lys Phe Leu Thr Gly Lys Tyr Phe Leu Leu Ala Gln
                100                 105                 110

Asn Gln Gln Gly Ser Thr Ser Gly Asp Gly Arg Thr Phe Phe
            115                 120                 125

Pro Phe Val Glu Ile Ser Phe Ile Ile Asp Asn Pro Asp Asn His
        130                 135                 140

Tyr His Ile Pro Leu Leu Leu Ser Asn Tyr Ser Tyr Thr Thr Tyr Arg
145                 150                 155                 160

Gly Ser
```

<210> SEQ ID NO 17
<211> LENGTH: 144
<212> TYPE: PRT
<213> ORGANISM: Gibberella zeae

<400> SEQUENCE: 17

```
Met Val Ser Pro Thr Lys Asp Pro Ile Thr Cys His Val Leu Asp Thr
 1                   5                  10                  15

Gln Ala Gly Lys Pro Ala Arg Gly Ile Arg Val Arg Leu Glu Gly Pro
             20                  25                  30

Ile Pro Pro Ser Ala Asn Pro His Ser Ala Ala Gln Pro Arg Ala Asn
         35                  40                  45

Thr Phe Glu Ser Ile Thr Asp Glu Asp Gly Arg Val Thr Ser Trp Leu
     50                  55                  60

Pro Phe Leu Ser Glu Asp Ser Ala Gly Glu Pro Pro Leu Gln Thr Leu
 65                  70                  75                  80

Val Glu Ile Leu Glu Asp Arg Lys Gly Arg Gly Ser Ser Arg Trp Thr
                 85                  90                  95

Leu Arg Phe Asp Thr Gly Ala Tyr Phe Gly Glu Asn Thr Phe Phe
                100                 105                 110

Pro Glu Val Thr Val Thr Phe Arg Met Glu Arg Gln Thr Tyr His
            115                 120                 125

Val Pro Leu Leu Leu Ser Pro Tyr Ser Tyr Thr Ser Tyr Arg Gly Ser
        130                 135                 140
```

<210> SEQ ID NO 18
<211> LENGTH: 144
<212> TYPE: PRT
<213> ORGANISM: Arabidopsis thaliana

<400> SEQUENCE: 18

```
Asp Arg Leu Arg Ile Ile Gly Gly His Leu Asn Val Ala Ala Glu Ala
 1                   5                  10                  15

Lys Ala Pro Lys Arg Ser Arg Pro Pro Ile Thr Thr His Val Leu Asp
             20                  25                  30

Val Ser Arg Gly Ala Pro Ala Ala Gly Val Glu Val His Leu Glu Val
         35                  40                  45

Trp Ser Gly Thr Thr Gly Pro Ser Phe Val His Gly Gly Gly Gly Val
```

```
                    50                  55                  60
Trp Ser Ser Val Gly Thr Ser Ala Thr Asp Arg Asp Gly Arg Ser Gly
 65                  70                  75                  80

Pro Leu Met Asp Leu Val Asp Ala Leu Asn Pro Gly Thr Tyr Arg Ile
                 85                  90                  95

Ser Phe Asp Thr Ala Lys Tyr Ser Pro Gly Cys Phe Phe Pro Tyr Val
                100                 105                 110

Ser Ile Val Phe Gln Val Thr Glu Ser Gln Lys Trp Glu His Phe His
            115                 120                 125

Val Pro Leu Leu Leu Ala Pro Phe Ser Phe Ser Thr Tyr Arg Gly Ser
130                 135                 140
```

<210> SEQ ID NO 19
<211> LENGTH: 154
<212> TYPE: PRT
<213> ORGANISM: Oryza sativa

<400> SEQUENCE: 19

```
Asp Arg Met Arg Ile Ile Gly Ala His Leu Gly Ser His Thr Gln His
 1               5                  10                  15

Ser Ala Asn Lys Ala Pro Glu Ile Thr Gly Ser Ser Asn Arg Thr Arg
                20                  25                  30

Pro Pro Ile Thr Thr His Val Leu Asp Val Ala Arg Gly Ser Pro Ala
             35                  40                  45

Ser Gly Ile Glu Val His Leu Glu Met Trp Lys Asp Ala Ser Thr Pro
         50                  55                  60

Pro Ser Phe Asn Asn Lys Asp Phe Asn Gly Trp Ala Thr Leu Gly Ser
 65                  70                  75                  80

Ser Val Thr Asn Asn Asp Gly Arg Ser Gly Gln Leu Met Asp Ile Val
                 85                  90                  95

Asn Asn Val Ala Pro Gly Phe Tyr Arg Ile Ser Phe Asn Thr Ser Lys
                100                 105                 110

Tyr Ala Pro Ser Gly Phe Phe Pro Tyr Val Ser Ile Ile Phe Glu Ile
            115                 120                 125

Lys Lys Asn Gln Thr Thr Glu His Phe His Val Pro Leu Leu His Ser
        130                 135                 140

Pro Phe Ser Phe Thr Thr Tyr Arg Gly Ser
145                 150
```

<210> SEQ ID NO 20
<211> LENGTH: 135
<212> TYPE: PRT
<213> ORGANISM: Streptomyces avermitilis

<400> SEQUENCE: 20

```
Met Ser Thr Ser Thr Thr Ala Ser Val Ser Thr His Ile Leu Asp Thr
 1               5                  10                  15

Ser Ile Gly Arg Pro Ala Ala Gly Val Ala Val Gln Leu Ala Ala Arg
                20                  25                  30

Ser Gly Arg Ser Ala Ser Tyr Gly Gln Gly Gly Asp Trp Gln Ala Leu
             35                  40                  45

Gly Gly Ser Ala Thr Asp Ala Asp Gly Arg Cys Lys Asp Leu Pro Ala
         50                  55                  60

Leu Pro Ala Gly Thr Thr His Val Arg Leu Asp Phe Ala Val Glu Pro
 65                  70                  75                  80

Tyr Phe Glu Lys Lys Gln Ala Asp Ala Gln Gln Asp Ala Pro Ala Asn
                 85                  90                  95
```

```
Arg Asp Ser Gly Ala Phe Phe Pro Glu Val Ala Ile Thr Phe Ala Val
            100                 105                 110

Lys Pro Gly Glu His Tyr His Val Pro Leu Leu Asn Pro Phe Gly
        115                 120                 125

Tyr Ser Val Tyr Arg Gly Ser
    130                 135

<210> SEQ ID NO 21
<211> LENGTH: 109
<212> TYPE: PRT
<213> ORGANISM: Nocardia farcinica

<400> SEQUENCE: 21

Met Ser Thr Pro Gly Thr Ser Thr Leu Ser Thr His Val Leu Asp Ala
1               5                   10                  15

Val Arg Gly Val Pro Ala Ala Gly Val Ala Val Thr Leu Tyr Ala Gly
            20                  25                  30

Ala Glu Pro Val Ala Ser Gly Ala Thr Asp Ala Asp Gly Arg Ile Gly
        35                  40                  45

Gly Leu Ala Glu Val Ser Pro Gly Thr Tyr Arg Leu Val Phe Asp Thr
    50                  55                  60

Gly Ala Tyr Phe Ala Ala Gln Gly Thr Pro Thr Phe Tyr Pro Glu Val
65                  70                  75                  80

Ala Ile Thr Phe Ala Val Thr Glu Glu Arg His His Val Pro Leu
                85                  90                  95

Leu Leu Ser Pro Phe Ala Phe Ser Thr Tyr Arg Gly Ser
            100                 105

<210> SEQ ID NO 22
<211> LENGTH: 111
<212> TYPE: PRT
<213> ORGANISM: Rubrobacter xylanophilus

<400> SEQUENCE: 22

Met Ser Gly Tyr Leu Thr Thr His Val Leu Asp Thr Ala Arg Gly Arg
1               5                   10                  15

Pro Ala Ala Gly Leu Glu Val Glu Leu Phe Arg Leu Ala Asp Gly Glu
            20                  25                  30

Arg Arg Leu Leu Lys Ala Thr Lys Thr Asn Ala Asp Gly Arg Thr Asp
        35                  40                  45

Glu Pro Leu Leu Glu Gly Glu Arg Phe Ala Arg Gly Thr Tyr Glu Leu
    50                  55                  60

Val Phe His Leu Gly Gly His Phe Gly Glu Ala Gly Phe Leu Asp Glu
65                  70                  75                  80

Val Pro Val Arg Phe Thr Val Glu Arg Pro Glu His Tyr His Val
                85                  90                  95

Pro Leu Leu Val Ser Pro Tyr Ser Tyr Thr Thr Tyr Arg Gly Ser
            100                 105                 110

<210> SEQ ID NO 23
<211> LENGTH: 119
<212> TYPE: PRT
<213> ORGANISM: Bacillus halodurans

<400> SEQUENCE: 23

Met Ser Gly Lys Val Thr Thr His Val Leu Asp Thr Ser Cys Gly Lys
1               5                   10                  15

Pro Ala Ala Gly Val Val Val Glu Leu Trp Arg Ile Val Glu Gly Gly
```

```
                20                  25                  30
Glu Ser Glu Leu Leu Thr Lys Ala Val Thr Asn Gln Asp Gly Arg Leu
            35                  40                  45

Asp Lys Pro Leu Leu Thr Glu Asn Lys Met Ala Arg Gly Val Tyr Glu
    50                  55                  60

Leu Arg Phe Gln Val Gly Asp Tyr Phe Leu Arg Asn Gly Phe Val Asn
65                  70                  75                  80

Gln Ala Tyr Pro Phe Leu His Val Ile Pro Val Arg Phe Gly Leu Glu
                85                  90                  95

Asp Val Asn Glu His Tyr His Val Pro Leu Leu Val Ala Pro Gly Gly
            100                 105                 110

Tyr Ser Thr Tyr Arg Gly Ser
            115

<210> SEQ ID NO 24
<211> LENGTH: 119
<212> TYPE: PRT
<213> ORGANISM: Deinococcus radiodurans

<400> SEQUENCE: 24

Met Ser Gly His Pro Gly Leu Thr Thr His Val Leu Asp Thr Ala Arg
1               5                   10                  15

Gly Lys Pro Ala Ala Gly Val Arg Val Gln Leu Cys Arg Val Thr Gly
                20                  25                  30

Asp Thr Arg Thr Pro Val Thr Glu Ala Val Thr Asn Ser Asp Gly Arg
            35                  40                  45

Thr Asp Ala Pro Leu Ile Glu Arg Gly Ser Leu Lys Gln Gly Thr Tyr
    50                  55                  60

Glu Leu Thr Phe His Val Ala Asp Tyr Phe Lys Gly Phe Val Ala Ala
65                  70                  75                  80

Ala Asp Pro Pro Phe Leu Asp Val Val Thr Leu Arg Phe Thr Val Gly
                85                  90                  95

Asp Thr Ser Gly His Tyr His Val Pro Leu Val Met Thr Pro Trp Ser
            100                 105                 110

Tyr Ser Thr Tyr Arg Gly Ser
            115

<210> SEQ ID NO 25
<211> LENGTH: 173
<212> TYPE: PRT
<213> ORGANISM: Canis familiaris

<400> SEQUENCE: 25

Met Asp Ile Glu Lys Val Asn Ser Met Asp Phe Gly Glu Phe Val Asp
1               5                   10                  15

Val Phe Gly Asn Val Ile Glu Arg Cys Pro Leu Ile Ala Ala Ala Val
                20                  25                  30

Trp Ser Gln Arg Pro Phe Ser Asn Leu Glu Asp Leu Glu Lys His Phe
            35                  40                  45

Phe Asp Phe Ile Asp Ala Leu Pro Gln Ser Gly Arg Glu Gly Ile Leu
    50                  55                  60

Arg Cys His Pro Asp Leu Ala Gly Arg Glu Leu Gln Gln Gly Thr Leu
65                  70                  75                  80

Ser Ala Glu Ser Arg Arg Glu Gln Ser Gly Ala Gly Leu Ala Ser Leu
                85                  90                  95

Asp Ala Asp Glu Arg Leu Arg Leu Ala Glu Leu Asn Ala Gln Tyr Arg
            100                 105                 110
```

-continued

Ala Arg Phe Gly Phe Pro Phe Val Leu Ala Ala Arg Arg Ser His Arg
            115                 120                 125

Ala Ala Val Pro Arg Glu Leu Ala Arg Arg Leu Arg Cys Pro Pro Ala
130                 135                 140

Gln Glu Leu Arg Thr Ala Leu Ala Glu Val Lys Lys Ile Gly His Leu
145                 150                 155                 160

Arg Leu Ala Asp Leu Leu Gly Thr Pro Pro Ala Arg Leu
            165                 170

<210> SEQ ID NO 26
<211> LENGTH: 175
<212> TYPE: PRT
<213> ORGANISM: Xenopus sp.

<400> SEQUENCE: 26

Met Asp Leu Asn Thr Ile Asn Ser Met Ser Tyr Glu Glu Phe Leu Asp
1               5                   10                  15

Ile Phe Gly Asn Ile Ile Glu Arg Cys Pro Ile Ile Thr Ala Ala Ile
            20                  25                  30

Trp Ser Gln Phe Pro Phe Ala Ser Val Thr Glu Leu Glu Asn Ser Val
            35                  40                  45

Tyr Asp Phe Ile Glu Ser Leu Pro Leu Thr Gly Lys Glu Gly Ile Leu
    50                  55                  60

Arg Cys His Pro Asp Leu Ala Gly Arg Asp Leu Met Arg Gly Thr Leu
65                  70                  75                  80

Thr Asp Glu Ser Gln Thr Glu Gln Ala Gln Ala Gly Leu Thr Ala Leu
                85                  90                  95

Thr Pro Lys Glu Arg Glu Thr Leu Asn Leu Leu Asn Ser Gln Tyr Lys
            100                 105                 110

Ala Lys Phe Gly Phe Pro Phe Val Ile Cys Ala Lys Met Ser Asp Lys
            115                 120                 125

Asn Lys Ile Met Arg Glu Leu Ala Ser Arg Leu Gln Asn Glu Gln Ser
130                 135                 140

Gln Glu Leu Gln Ile Gly Ile Ala Glu Val Lys Lys Ile Cys His Leu
145                 150                 155                 160

Arg Val Asn Asp Leu Phe Leu Asn Val Lys Leu Pro Thr Lys Leu
            165                 170                 175

<210> SEQ ID NO 27
<211> LENGTH: 173
<212> TYPE: PRT
<213> ORGANISM: Takifugu rubripes

<400> SEQUENCE: 27

Met Asp Ile Arg Ala Val Asn Asp Leu Ser Phe Glu Glu Phe Val Asn
1               5                   10                  15

Ile Phe Gly Asn Leu Val Glu Lys Cys Pro Ile Val Ala Ala Thr Val
            20                  25                  30

Trp Ser Glu Arg Pro Phe Gly Ser Phe Thr Ala Leu Glu Lys Ala Ile
            35                  40                  45

His Asp Phe Ile Asp His Leu Pro Gln Ser Gly Lys Glu Gly Leu Leu
    50                  55                  60

Arg Cys His Pro Asp Leu Ala Gly Arg Asp Leu Gln Arg Gly Thr Leu
65                  70                  75                  80

Thr Gln Glu Ser Arg Val Glu Gln Val Ala Ala Gly Leu Asp Ala Leu
                85                  90                  95

-continued

```
Gly Ser Glu Glu Ala Ser Arg Met Glu Arg Leu Asn Asp Glu Tyr Lys
                100                 105                 110

Gln Arg Phe Gly Phe Pro Phe Val Ile Cys Ala Arg Met Asn Asp Lys
            115                 120                 125

Ala Thr Ile Leu His Gln Met Thr Glu Arg Cys Gln Asn Glu Pro Ala
        130                 135                 140

Leu Glu Thr Leu Arg Gly Ile Glu Glu Val Lys Lys Ile Ser Ser Leu
145                 150                 155                 160

Arg Leu His Ser Ile Ile Leu Val Asp Thr Pro Arg Leu
                165                 170

<210> SEQ ID NO 28
<211> LENGTH: 174
<212> TYPE: PRT
<213> ORGANISM: Danio rerio

<400> SEQUENCE: 28

Met Asp Ile Asn Val Val Asn Ala Leu Ala Tyr Glu Asp Phe Val Lys
1               5                   10                  15

Leu Phe Gly Asn Val Val Glu Lys Cys Pro Leu Ile Ser Ala Ala Ile
            20                  25                  30

Trp Ser Tyr Arg Pro Phe Lys Asp Leu Ala Asp Ile Glu Ala Arg Ile
        35                  40                  45

Ser Glu Phe Ile His Ser Leu Pro Asp Ser Gly Lys Glu Gly Ile Leu
    50                  55                  60

Arg Cys His Pro Asp Leu Ala Gly Arg Asp Leu Gln Ser Gly Thr Leu
65                  70                  75                  80

Thr Pro Glu Ser Gln Glu Gln Ser Gln Ala Gly Met Thr Thr Leu
                85                  90                  95

Asp Ser Ala Glu Ile Val His Met Tyr Arg Leu Asn Ser Glu Tyr Lys
                100                 105                 110

Glu Arg Phe Gly Phe Pro Phe Val Ile Cys Ala Arg Leu Asn Asn Lys
            115                 120                 125

Ala Asp Ile Val Arg Gln Leu Ser Glu Arg Leu Lys Asn His Arg Thr
        130                 135                 140

Ala Glu Arg Glu Arg Ala Ile Glu Glu Val Lys Lys Ile Cys Ser Leu
145                 150                 155                 160

Arg Leu His Asn Ile Val Leu Ser Asp Ile Gln Thr Lys Leu
                165                 170

<210> SEQ ID NO 29
<211> LENGTH: 182
<212> TYPE: PRT
<213> ORGANISM: Strongylocentrotus sp.

<400> SEQUENCE: 29

Met Ala Glu Lys Phe Thr Ile Glu Ala Ile Asn Gln Gln Glu Tyr Glu
1               5                   10                  15

Glu Phe Ile Glu Asn Phe Glu Ile Leu Asp Glu His Gly Ile Leu Ile
            20                  25                  30

Ala Gly Ala Val Trp Ser His Arg Pro Phe Gln Ser Phe Asp His Leu
        35                  40                  45

His Arg Cys Phe Cys Asp Phe Met Asp Ser Leu Pro Glu Ser Gly Lys
    50                  55                  60

Gln Ser Ile Leu Arg Cys His Pro Asn Leu Ala Gly Lys Leu Ala Arg
65                  70                  75                  80

Gln Gly Lys Leu Thr Ser Glu Ser Glu Gln Glu Gln Ala Ser Ala Gly
```

```
                    85                  90                  95
Leu Ser Ser Leu Thr Asp Glu Gln Tyr Asn Glu Ile His Lys Asn Asn
                100                 105                 110

Asp Ile Tyr Arg Lys Lys Phe Ser Phe Pro Phe Val Ile Cys Ala Arg
            115                 120                 125

Glu Asn Lys Ile Ala Ala Ile Leu Gln Gly Leu Gln Thr Arg Ile Gln
        130                 135                 140

Asn Ala Arg Glu Leu Glu Leu Gln Lys Gly Ile Glu Glu Val Lys Lys
145                 150                 155                 160

Ile Ser Tyr Tyr Arg Leu Leu Asp Met Ile Gln Glu Lys Thr Leu Ser
                165                 170                 175

Pro Lys Lys Pro Lys Leu
            180
```

<210> SEQ ID NO 30
<211> LENGTH: 186
<212> TYPE: PRT
<213> ORGANISM: Candida albicans

<400> SEQUENCE: 30

```
Met Ala Leu Pro Thr Ile Glu Ser Phe Lys Arg Leu Ser Ser Lys Asp
1               5                   10                  15

Lys Arg Gln Val Leu Asp His Leu Phe Glu Pro Cys Asn Thr Leu Ser
            20                  25                  30

Asn Phe Ile Phe Ile Lys Val Leu His Gln Gln Tyr Asn Thr Tyr Pro
        35                  40                  45

Glu Phe Ile Asn Leu Val Arg Lys Glu Leu Leu Glu Phe Leu Lys Gln
    50                  55                  60

Ser Glu Thr Phe Gln Ser Gln Tyr Gln Gly Ile Asn Pro Val Ile
65                  70                  75                  80

Asn Glu Ile Ile Ser Ala His Pro Arg Leu Gly Glu Pro Lys Lys Glu
                85                  90                  95

Thr Leu Ser Val His Ser Asn Asn Glu Gln Lys Thr Leu Asn Asn Asp
            100                 105                 110

Pro Glu Ile Ile Lys Lys Leu Lys Glu Leu Asn Ala Ala Tyr Glu Lys
        115                 120                 125

Thr Phe Pro Gly Leu Arg Tyr Val Val Phe Val Asn Gly Arg Ser Arg
    130                 135                 140

His Glu Ile Met Asp Asn Met Gln Lys Arg Ile Glu Arg Asn Asp Ile
145                 150                 155                 160

Asn Leu Glu Arg Val Glu Ala Phe Asn Ala Met Cys Asp Ile Ala Leu
                165                 170                 175

Asp Arg Ala Asn Lys Leu Gly Ile Lys Leu
            180                 185
```

<210> SEQ ID NO 31
<211> LENGTH: 175
<212> TYPE: PRT
<213> ORGANISM: Gibberella zeae

<400> SEQUENCE: 31

```
Met Thr Leu Leu Pro Pro Lys Glu Leu Arg Ile Ala Asn Glu Thr Glu
1               5                   10                  15

Gln Ile Lys Thr Leu Asp Leu Leu Phe Glu Pro Ser Pro Ala Ile His
            20                  25                  30

Ser Thr Leu Ile Pro Val Leu Arg Glu Ser Glu Tyr Thr Ser Tyr Pro
        35                  40                  45
```

```
Glu Leu Ile Asp Ala Cys Arg Ser Arg Leu Val Ser Leu Ala Ser Ser
    50                  55                  60

Ser Ser Pro Thr Asn Pro Asp Ala Thr Leu Leu Ser Ile Leu Gly Ser
65                  70                  75                  80

His Pro Arg Leu Gly Ala Lys Lys Val Glu Ser Ala Gln Ser Ala Ala
                85                  90                  95

Glu Gln Ala Asn Leu Gln Gly Gln Gly Glu Leu Ala Lys Leu Asn
            100                 105                 110

Gln Glu Tyr Glu Glu Lys Phe Pro Gly Leu Arg Tyr Val Val Phe Val
        115                 120                 125

Asn Gly Arg Gly Arg Pro Glu Ile Met Glu Asn Met Lys Ala Arg Ile
    130                 135                 140

Ser Arg Gly Val Phe Ser Lys Glu Val Ala Glu Ala Leu Gln Ala Met
145                 150                 155                 160

Cys Asp Ile Ala Lys Asp Arg Ala Ser Lys Leu Asp Ala Lys Leu
                165                 170                 175

<210> SEQ ID NO 32
<211> LENGTH: 177
<212> TYPE: PRT
<213> ORGANISM: Arabidopsis thaliana

<400> SEQUENCE: 32

Met Ala Met Glu Ile Gly Glu Asp Glu Trp Lys Val Cys Cys Gly Ser
1               5                   10                  15

Ser Glu Phe Ala Lys Gln Met Ser Thr Ser Gly Pro Leu Thr Ser Gln
            20                  25                  30

Glu Ala Ile Tyr Thr Ala Arg Asp Ile Trp Phe Asn Gln Val Asn Val
        35                  40                  45

Thr Asp Trp Leu Glu Ala Phe Ser Ala His Pro Gln Ile Gly Asn Thr
    50                  55                  60

Pro Ser Pro Ser Ile Asn Ser Asp Phe Ala Arg Arg Ser Val Ser Glu
65                  70                  75                  80

Gln Ser Thr Ala Phe Ala Thr Thr Ser Ala Ser Ala Leu Gln Glu Leu
            85                  90                  95

Ala Glu Trp Asn Val Leu Tyr Lys Lys Lys Phe Gly Phe Ile Phe Ile
        100                 105                 110

Ile Cys Ala Ser Gly Arg Thr His Ala Glu Met Leu His Ala Leu Lys
    115                 120                 125

Glu Arg Tyr Glu Asn Arg Pro Ile Val Glu Leu Glu Ile Ala Ala Met
    130                 135                 140

Glu Gln Met Lys Ile Thr Glu Leu Arg Met Ala Lys Leu Phe Ser Asp
145                 150                 155                 160

Lys Ala Lys Val Ile Ser Glu Thr Asp Ser Ser Ser Pro Val Ser
                165                 170                 175

Thr

<210> SEQ ID NO 33
<211> LENGTH: 176
<212> TYPE: PRT
<213> ORGANISM: Oryza sativa

<400> SEQUENCE: 33

Met Ala Thr Thr Arg Gly Gln Leu Pro Val Glu Asp Val Leu Arg Val
1               5                   10                  15

Asn Gly Ser Arg Arg Phe Ala Ala Ala Leu Ala Ala Ala Ser Pro Phe
```

```
            20                  25                  30
Ala Ser Leu Ala Asp Ala Leu Leu Ala Ala Arg Arg Ile Trp Leu Asn
        35                  40                  45

Glu Val Asp Val Asn Gly Trp Leu Glu Ala Phe Ala Ala His Pro Ala
    50                  55                  60

Ile Gly Thr Thr Ser Ser Ala Pro Lys Trp Cys Lys Glu Glu Gln
65                  70                  75                  80

Ser Ala Ala Leu Ala Thr Ala Thr Asp Ser Thr Ala Gln Glu Leu Ala
                85                  90                  95

Asp Trp Asn Ala Arg Tyr Arg Glu Lys Phe Gly Phe Val Phe Met Ile
            100                 105                 110

Cys Ala Ser Gly Arg Thr Ala Pro Glu Val Leu Ala Glu Leu Lys Arg
        115                 120                 125

Arg Tyr Glu Asn Arg Pro Ile Val Glu Leu Glu Ile Ala Ala Gln Glu
    130                 135                 140

Glu Leu Lys Ile Thr Glu Leu Arg Leu Ala Lys Leu Phe Ala Ser Glu
145                 150                 155                 160

Pro Val Ala Pro Pro Ser Ser Thr Val Gly Gly Pro Thr Ser Gln Ser
                165                 170                 175

<210> SEQ ID NO 34
<211> LENGTH: 172
<212> TYPE: PRT
<213> ORGANISM: Streptomyces avermitilis

<400> SEQUENCE: 34

Met Thr Ser Thr Ser Thr Pro Pro Gly Leu Ala Arg Phe Asn Asp Leu
1               5                   10                  15

Gly Glu His Ala Ala Leu Ala Ala Leu His Glu Ala Cys Ala Ser Thr
            20                  25                  30

Thr Trp Ala Arg Arg Leu Ile Ala Ala Arg Pro Tyr Ala Thr Ala Asp
        35                  40                  45

Asp Leu Tyr Thr Ala Ser Asp Ala Ala Met Ala Glu Leu Thr Ala Ala
    50                  55                  60

Asp Leu Ala Gln Ala Met Ala Gly His Pro Pro Ile Gly Arg Pro Lys
65                  70                  75                  80

Pro Gly Asp Pro Thr Ser Ala Arg Glu Gln Arg Gly Met Ala Gly Ala
                85                  90                  95

Ser Glu Glu Leu Lys Ala Asp Met Leu Glu Leu Asn Leu Ala Tyr Gln
            100                 105                 110

Glu Lys Phe Gly His Val Phe Leu Ile Cys Ala Thr Gly Arg Thr Gly
        115                 120                 125

Glu Gln Met Arg Asp Ala Val Arg Glu Arg Ile Gly Asn Ala Pro Glu
    130                 135                 140

Arg Glu Arg Glu Ile Val Arg Thr Glu Leu Gly Lys Ile Asn Arg Ile
145                 150                 155                 160

Arg Leu Ala Arg Leu Val Glu Glu Asp Ala His Ala
                165                 170

<210> SEQ ID NO 35
<211> LENGTH: 172
<212> TYPE: PRT
<213> ORGANISM: Nocardia farcinica

<400> SEQUENCE: 35

Met Thr His Pro Ala Pro Ala Gly Ile Ala Ala Phe Asp Ala Leu Pro
1               5                   10                  15
```

Ala Ala Ala Ala Thr Ala Ala Leu Leu Glu Val Cys Ala Ser Pro Glu
            20                  25                  30

Trp Ala Arg Arg Val Val Ala Gly Arg Pro Tyr Gly Thr Ala Glu Arg
        35                  40                  45

Leu Tyr Ala Ala Ala Glu Arg Val Leu Ala Asp Leu Pro Glu Arg Glu
    50                  55                  60

Ile Asp Arg Ala Leu Ala Gly His Pro Arg Ile Gly Glu Gln Pro Gly
65                  70                  75                  80

Gly Ala Ala Ala Ser His Glu Gln Ala Gly Val Ala Gly Ala Asp Ala
                85                  90                  95

Ala Thr Arg Ala Ala Leu Ala Ala Gly Asn Arg Ala Tyr Glu Arg Arg
            100                 105                 110

Phe Gly Arg Ile Tyr Leu Val Ser Ala Ala Gly Arg Ser Ala Asp Glu
        115                 120                 125

Leu Leu Ala Ile Leu Glu Ala Arg Leu Arg Asn Asp Pro Glu Val Glu
    130                 135                 140

Thr Arg Val Leu Arg Glu Glu Leu Ala Lys Ile Asn Arg Leu Arg Leu
145                 150                 155                 160

Gly Arg Leu Pro Ala Val Thr Gly Glu Asp Pro Val
                165                 170

<210> SEQ ID NO 36
<211> LENGTH: 177
<212> TYPE: PRT
<213> ORGANISM: Bacillus halodurans

<400> SEQUENCE: 36

Met Met Gly Met Ala Val Ser Thr Lys Leu Ser Ile Asp Glu Val Asn
1               5                   10                  15

Met Leu Glu Lys Glu Asp Phe Val Thr Lys Ile Gly Pro Ile Phe Glu
            20                  25                  30

His Ser Pro Trp Val Ala Glu Arg Ala Trp Ala His Arg Pro Phe Thr
        35                  40                  45

Ser Ala Glu Asn Met Tyr Glu Cys Met Leu Glu Lys Val Tyr Glu Ala
    50                  55                  60

Asp Lys Arg Leu Gln Leu Ala Leu Leu Arg Ala His Pro Asp Leu Gly
65                  70                  75                  80

Thr Arg Leu Glu Ile Ser Glu Thr Ser Gln Ser Glu Gln Arg Ala
            85                  90                  95

Gly Leu Ser Gln Leu Thr Glu Glu Phe Ala Val Phe Ala Glu Leu
            100                 105                 110

Asn Lys Cys Tyr Val Asp Thr Phe Arg Phe Pro Phe Ile Met Ala Val
        115                 120                 125

Arg Gly Gln Thr Lys Asn Ser Ile Lys Glu Gln Met Arg Lys Arg Leu
    130                 135                 140

Val Asn Asp Glu Glu Gln Arg Lys Thr Ala Leu Arg Glu Val Ala
145                 150                 155                 160

Lys Ile Ala Lys Phe Arg Leu Ala Asp Leu Val Val Met Gly Ser Arg
                165                 170                 175

Ser

<210> SEQ ID NO 37
<211> LENGTH: 188
<212> TYPE: PRT
<213> ORGANISM: Deinococcus radiodurans

```
<400> SEQUENCE: 37

Met Thr Arg Thr Pro Leu Thr Leu Glu Gln Leu Asn Ala Leu Ser Asp
1               5                   10                  15

Asp Ala Phe Thr Glu His Phe Ala Gly Val Leu Glu His Ser Pro His
            20                  25                  30

Tyr Ala Arg Arg Ala Ala Gly Arg Pro Phe Ala Asp Val Glu Glu
        35                  40                  45

Val Ala Ala Ala Phe Ala Arg Ala Val Ala Ala Asp Glu Pro Gly Ala
    50                  55                  60

Gln Val Gln Leu Ile Arg Ala His Pro Asp Leu Ala Gly Lys Ala Ala
65                  70                  75                  80

Leu Ala Gly Glu Leu Thr Ala Glu Ser Ala Ser Glu Gln Thr Ser Ala
                85                  90                  95

Gly Leu Asp Arg Leu Ser Pro Glu Glu Tyr Ala Glu Phe Gln Arg Leu
            100                 105                 110

Asn Ala Ala Tyr His Glu Arg Phe Gly Leu Pro Tyr Val Val Cys Val
            115                 120                 125

Arg Glu Asn Thr Lys Asp Thr Ile Phe Glu Gly Ala Arg Arg Leu
            130                 135                 140

Thr His Thr Gln Glu Glu Gln Ala Ala Leu His Glu Ile Gly
145                 150                 155                 160

Arg Ile Ala Arg Leu Arg Ile Leu Asp Leu Val Gln Glu Gly Arg Gln
                165                 170                 175

Glu Lys Arg Met Asp Gly Arg Leu Ile Arg Ile Pro
            180                 185

<210> SEQ ID NO 38
<211> LENGTH: 4
<212> TYPE: PRT
<213> ORGANISM: Unknown
<220> FEATURE:
<223> OTHER INFORMATION: Description of Unknown: Conserved
      carboxy-terminal tetrapeptide

<400> SEQUENCE: 38

Tyr Arg Gly Ser
1

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      consensus peptide
<220> FEATURE:
<221> NAME/KEY: MOD_RES
<222> LOCATION: (3)..(4)
<223> OTHER INFORMATION: Any amino acid
<220> FEATURE:
<221> NAME/KEY: MOD_RES
<222> LOCATION: (6)..(7)
<223> OTHER INFORMATION: Any amino acid

<400> SEQUENCE: 39

Arg Leu Xaa Xaa Ile Xaa Xaa His Leu
1               5
```

METHOD FOR CONVERSION OF URIC ACID TO ALLANTOIN AND RELATED ENZYMES

CROSS-REFERENCE TO RELATED APPLICATIONS

This application is a 371 of PCT/IT2006/000778, filed Nov. 7, 2006, which claims the benefit of U.S. Provisional Application Ser. No. 60/734,327, filed Nov. 7, 2005, the contents of each of which are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 11, 2012, is named 1281020.txt and is 49,581 bytes in size.

INTRODUCTION

Purines, which are among the building blocks of nucleic acids, are degraded in animals to waste nitrogenous substances (Vogels and Van der Drift, 1976, *Bacteriol Rev,* 2, 403-468; Stryer, 1995, 755-788). The first step of the general purine degradation pathway is the oxidation of the nitrogenous base xanthine to uric acid by the enzyme xanthine oxidase; in most mammals, uric acid is further oxidized to allantoin which is then excreted by kidney. The biological conversion of uric acid requires the enzyme uricase or urate oxidase (urate-oxygen oxidoreductase: EC 1.7.3.3). Humans, because of the lack of this enzyme, are unable to degrade uric acid and excrete this compound as the end product of purine degradation (Oda et al., 2002, *Mol Biol Evol,* 5, 640-653). As a consequence, humans have high levels of uric acid in the blood, approximately 0.3 mM. This condition is thought to have beneficial effects because uric acid is an effective scavenger of potentially harmful free radicals (Ames et al., 1981, *Proc Natl Acad Sci USA,* 11, 6858). However, since uric acid is scarcely soluble, high levels of uric acid (hyperuricemia) can cause significant health problems, leading to kidney stones when it builds up in the kidneys and to gout when crystals accumulate in the joints. Both genetic and environmental factors are recognized as contributing to the development of hyperuricemia (Wortmann, 2002, *Curr Opin Rheumatol,* 3, 281-6). Other causative agents of hyperuricemia are certain malignancies: acute severe hyperuricemia is a major complication of the Tumor Lysis Syndrome (TLS), a constellation of metabolic disturbances that can occur spontaneously, but most often is seen after chemotherapy (Locatelli and Rossi, 2005, *Contrib Nephrol,* 61-8). Hyperuricemia is treated pharmacologically by reducing the blood levels of uric acid (Schlesinger, 2004, *Drugs,* 21, 2399-416; Pea, 2005, *Contrib Nephrol,* 35-46). A thromboxane synthetase inhibitor and a thromboxane receptor antagonist have been described in the patent application EP 0 449 764 as potential reducing serum uric acid agents. In addition, the patent application JP6172185 discloses new xanthine oxidase inhibitor extracted from fresh eucalyptus leaves and able to suppress uric acid production in vivo.

The treatment of hyperuricemia can be achieved by means of three different ways: (1) by reducing uric acid production through the inhibition of xanthine oxidase (uricostatic drugs); (2) by increasing uric acid clearance through an inhibition of its renal tubular reabsorption (uricusuric drugs); (3) through metabolic conversion of uric acid to a more soluble compound (uricolytic drugs). Uricostatic agents (as allopurinol) and uricusuric agents (as probenecid) are widely used for the treatment of hyperuricemia. However, allopurinol induces pharmacokinetic interactions with other drugs and is not well tolerated by about 5% of the patients, while probenecid can not be used in presence of renal calculi or renal insufficiency. Moreover, these agents can be poorly effective in the treatment of acute hyperuricemia occurring in TLS. Alternative treatment of hyperuricemia includes the use of uricolytic drugs, which are based on urate oxidase. Different forms of urate oxidase are employed in uricolytic drugs: (1) natural *Aspergillus flavus* urate oxidase: Uricozyme from Sanofi-Synthelabo; (2) recombinant urate oxidase expressed in *S. cerevisiae*: rasburicase, Fasturtec/Elitek, from Sanofi-Synthelabo; (3) pegylated recombinant porcine urate oxidase: PEG-uricase from Savient Pharmaceuticals. The enzyme urate oxidase promotes the conversion of uric acid into allantoin, a compound that is 10 times more soluble than uric acid and is therefore excreted easily. In several clinical trials, uricolytic agents have shown to be very effective in preventing and treating hyperuricemia, and they are considered elective urate-lowering agents for TLS (Locatelli and Rossi, 2005, *Contrib Nephrol,* 61-8).

The biochemistry of uricolytic drugs, however, is still ill-defined. The true product of the urate oxidase reaction is not allantoin, but 5-hydroxyisourate (HIU); HIU is an unstable compound (with a half-life of about 20 minutes) that can decay spontaneously to 2-oxo-4-hydroxy-4-carboxy-5-ureidoimidazoline (OHCU); OHCU is in turn unstable and can decay spontaneously to give racemic allantoin as a stable end product (Modric et al., 1992, *Tetrahedron Letters,* 44, 6691-6694; Kahn et al., 1997, *J. Am. Chem. Soc.,* 119, 5435-5442). By contrast, however, only the dextrorotatory form of allantoin S(+)-allantoin, appears to be formed in living cells (Vogels and Van der Drift, 1976, *Bacteriol Rev,* 2, 403-468). Moreover, the intermediates of the urate oxidase reaction are reactive species (Santos et al., 1999, *Arch Biochem Biophys,* 2, 285-294), and can lead to different, sometime toxic end-products depending on the reaction environment (Priest and Pitts, 1972, *Anal Biochem,* 1, 195-205; Bongaerts and Vogels, 1979, *Biochim Biophys Acta,* 2, 295-308). For these reasons, the putative presence of additional enzymes in the biological conversion of uric acid to S(+)-allantoin has been postulated for a long time. Polypeptides able to facilitate hydrolysis of HIU have been described in *Glycine max* and *Bacillus subtilis*; in all cases, however, racemic allantoin was observed as the final output of the reaction (Sarma et al., 1999, *J Biol Chem,* 48, 33863-33865; Lee et al., 2005, *FEBS Lett,* 21, 4769-4774). Indeed, an enzymatic system able to efficiently and selectively convert uric acid into the natural stereoisomer of allantoin has never been described.

DESCRIPTION OF THE INVENTION

Here the authors show that all living organisms that convert uric acid to allantoin possess, in addition to urate oxidase, two specific enzymes (hereafter called HIU hydrolase and OHCU decarboxylase) able to catalyse the conversion of the urate oxidation products to S(+)-allantoin. The authors disclose a method for obtaining recombinant HIU hydrolase and OHCU decarboxylase from mouse genes (hereafter called MuraH and MuraD, respectively), and they demonstrate the catalytic activity of these enzymes in the conversion of uric acid into S(+)-allantoin. Through phylogenetic genome comparison, the authors also demonstrate that the genes belonging to the HIU hydrolase and OHCU decarboxylase families defined here are selectively required in all organisms able to degrade uric acid. This implies that the homologous variants of MuraH and MuraD are expected to have the same catalytic activity and function. Indeed, genes encoding HIU hydrolase and OHCU decarboxylase are found in a wide range of organisms, comprising mammals. Humans, however, have lost functional copies of the genes encoding these enzymes along with urate oxidase during the evolution of primate ancestors. Therefore, the administration of these enzymes together with urate oxidase could allow a much faster and safer conversion of urate oxidation products into allantoin, and thus a more effective and safe treatment of hyperuricemia.

Therefore it is an object of the present invention a polypeptide molecule able to selectively modulate uric acid conversion into S(+)-allantoin.

In an embodiment, the polypeptide catalyses the conversion of 5-hydroxyisourate (HIU) into 2-oxo-4-hydroxy-4-carboxy-5-ureidoimidazoline (OHCU). More preferably, the polypeptide has an 5-hydroxyisourate (HIU) hydrolase activity. In particular, the polypeptide is comprised in the following amino acid sequence (SEQ ID NO: 2) or in the sequence of functional or ortholog encoded variants thereof:

```
M A T E S S P L T T H V L D T A S G L P
A Q G L C L R L S R L E A P C Q Q W M E
L R T S Y T N L D G R C P G L L T P S Q
I K P G T Y K L F F D T E R Y W K E R G
Q E S F Y P Y V E V V F T I T K E T Q K
F H V P L L L S P W S Y T T Y R G S
```

In particular, the polypeptide essentially consists in the amino acid sequence of SEO ID NO: 2 or in the sequence of functional or ortholog encoded variants thereof.

In an alternative embodiment, the polypeptide catalyses the conversion of 2-oxo-4-hydroxy-4-carboxy-5-ureidoimidazoline (OHCU) into S(+)-allantoin. In particular, it has an 2-oxo-4-hydroxy-4-carboxy-5-ureidoimidazoline (OHCU) decarboxylase activity. Preferably, the polypeptide is comprised in the following amino acid sequence (SEQ ID NO: 4) or in the sequence of functional or ortholog encoded variants thereof:

```
M D M V K V N S M D F G E F V D V F G N
I V E K C P L I A A A V W S Q R P F S G
L E D L E N H F F A F I D A L P R S G Q
E G I L R C H P D L A G R D L Q Q G T L
T A E S Q R E Q S Q A G L T S L D T D D
R L R L Q Q L N A Q Y R E R F G F P F V
L A A R L S D R A T V P R E L A R R L Q
C Q P E S E L R T A L G E V K K I S H L
R L T D L L G A H S H S A R V E L P
```

More preferably, the polypeptide according essentially consists in the amino acid sequence of (SEQ ID NO: 4) or in the sequence of functional or ortholog encoded variants thereof.

It is a further object of the invention, a pharmaceutical composition for treating uric acid related disorders comprising at least one of the polypeptide described above or pharmacologically active fragment thereof together with appropriated excipients. In particular, the pharmaceutical composition comprises a polypeptide comprised in the amino acid sequence of (SEQ ID NO: 2) or in the sequence of functional or ortholog encoded variants thereof or pharmacologically active fragment thereof and a polypeptide comprised in the amino acid sequence of (SEQ ID NO: 4) or in the sequence of functional or ortholog encoded variants thereof or pharmacologically active fragment thereof with appropriated excipients. Preferably, the pharmaceutical composition further comprises a pharmacologically active amount of urate oxidase.

It is another object of the invention, the polypeptide described above for medical use. In particular for the treatment of uric acid related disorders. Preferably, the uric acid related disorder is hyperuricemia. More preferably, the hyperuricemia is induced by Tumor Lysis Syndrome.

An ulterior object of the invention is a process to selectively modulate uric acid conversion into S(+)-allantoin comprising the step of incubating uric acid in appropriate condition with at least one of the polypeptide described above.

The invention will be now described by means of non limiting examples, making reference to the following figures:

BRIEF DESCRIPTION OF THE FIGURES

FIG. 5 Sequence comparison of selected members of the HIU hydrolase family (COG2351). Amino acid conservation is visualized according to the ESPript (Gouet et al., 1999, *Bioinformatics*, 4, 305-308) equivalence measure, with a similarity threshold set to emphasize strictly conserved positions. Invariant residues are boxed in red; physico-chemical equivalent residues are boxed in yellow (HKR polar positive; DE polar negative; STNQ polar neutral; AVLIM non polar aliphatic; FYW non polar aromatic). Conserved positions corresponding to the PTS2 consensus are boxed in green; the starting methionine of mouse alternative transcripts is marked with a red arrow. FIG. 5 discloses SEQ ID NOs: 9-24, respectively, in order of appearance.

FIG. 7 Sequence comparison of selected members of the OHCU decarboxylase family (COG3195). Amino acid conservation is visualized according to the ESPript (Gouet, Courcelle et al., 1999, *Bioinformatics*, 4, 305-308) equivalence measure, with a similarity threshold set to emphasize strictly conserved positions. Invariant residues are boxed in red; physico-chemical equivalent residues are boxed in yellow (HKR polar positive; DE polar negative; STNQ polar neutral; AVLIM non polar aliphatic; FYW non polar aromatic); carboxy-terminal tripeptides corresponding to the PTS1 consensus are boxed in green; the shown *Arabidopsis thaliana* sequence is encoded by the same gene also encoding HIU hydrolase. FIG. 7 discloses SEQ ID NOs: 4 and 25-37, respectively, in order of appearance.

METHODS

Bioinformatics

Figure 1:
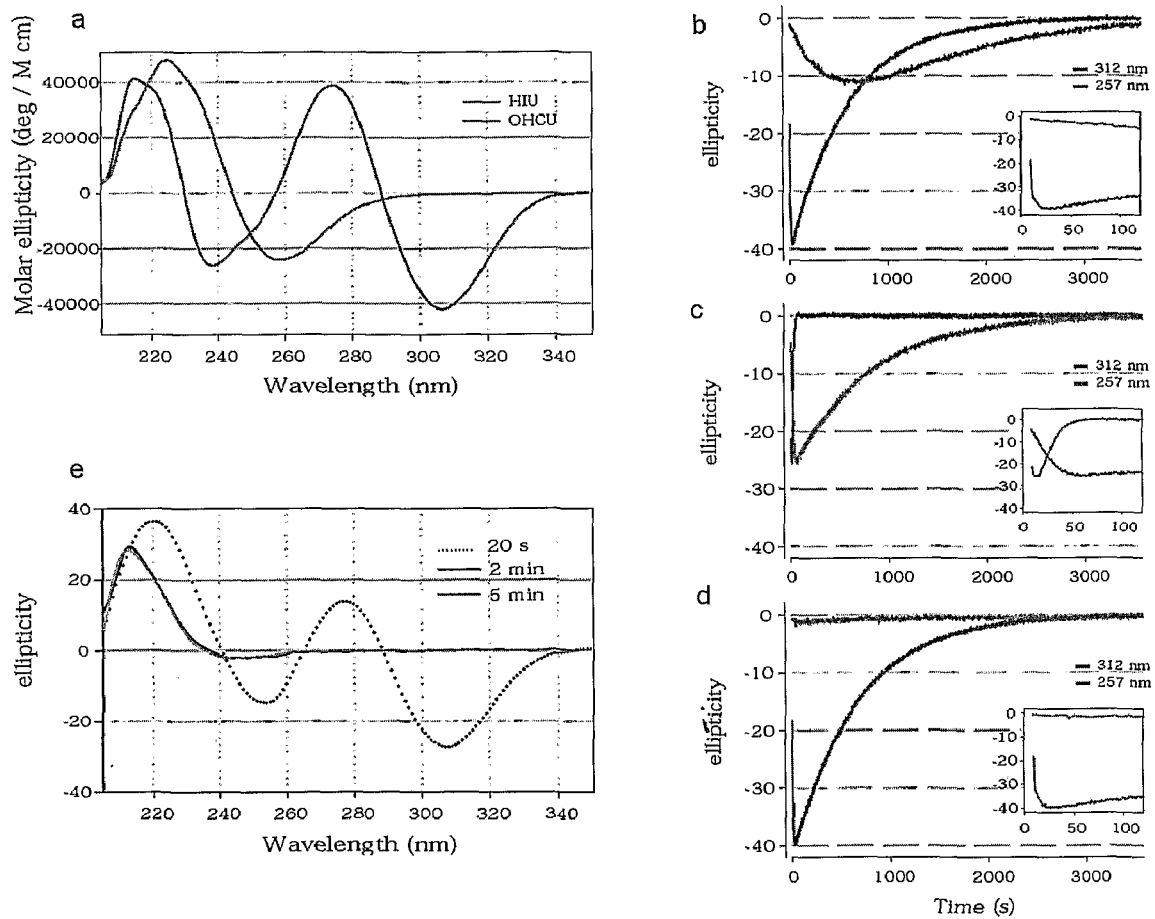
FIG. 1. Biochemical function of 5-hydroxyisourate (HIU) hydrolase and 2-oxo-4-hydroxy-4-carboxy-5-ureidoimidazoline (OHCU) decarboxylase in uric acid degradation as characterized by circular dichroism (CD) measurements; a) CD spectra of HIU and OHCU (pH 7.6, 25°, 0.1M sodium phosphate); b-d) Time courses monitored by CD measurements at 312 nm (HIU, blue curves) and 257 nm (OHCU, red curves) of the urate conversion catalyzed by b) UO, c) UO+MuraH, d) UO+MuraD; insets represent the first 120 seconds of the time courses; f) time-resolved CD spectra of the enzymatic product of urate conversion with UO+MuraH+MuraD.

Initial search for genes related to UO was conducted at the NCBI (http://www.ncbi.nlm.nih.gov) by visual inspection of the bacterial genomic loci of UO. Assignment of genes to COGs and a rough estimate of organism distributions was obtained with the BLink ("BLAST Link") utility. After restricting the search to a small number of candidate families, presence of family members in complete genomes was assessed by blastp and tblastn searches; organism distributions was examined in details and compared to the distribution of UO genes to infer correlated events of gene loss and gain (Barker and Pagel, 2005, *PLoS Comput Biol*, 1, e3). Automated search of functional association was performed with the String (von Mering et al., 2005, *Nucleic Acids Res*, Database issue, D433-437) web server (http://string.embl.de) using in input the UO family (COG3648) and selecting "neighbourhood", "gene fusion", and "co-occurrence" as association criteria. Definition of the precise coding sequence boundaries for eukaryotic members of the two gene families resulting from these analysis was based on protein HMM and EST comparisons using Genewise and Estwise (http://www.ebi.ac.uk/Wise2); this procedure helped identifying the short exon encoding the PTS2 signal and of transcriptional variants in COG2135. Distinction among genes and pseudogenes was made in eukaryotic sequences based on integrity of the coding sequence, EST evidence, and Ka/Ks measurements; in cases in which no convincing evidence was obtained, the gene was marked as "uncertain". Sequence alignments were generated with the Clustalw program.

Materials

All reagents were from Sigma unless otherwise indicated, and used without further purification. IMAGE clones used for recombinant expression of MuraH (ID: 6747242) and MuraD (ID: 748078) were obtained from RZPD (Deutsches Ressourcenzentrum für Genomforschung). Uniformly labelled $^{15}N,^{13}C$ uric acid was synthesised enzymatically from $[^{15}N,^{13}C]$-r-adenosine (Spectra Stable Isotopes) with the following protocol: 4 mg of labelled adenosine were dissolved in 1 ml buffer 0.1 M potassium phosphate pH 7.6 with addition of adenosine deaminase (5 U); after 5 min, nucleoside phosphorylase (5 U), xanthine oxidase (8 U), and catalase (5 U) were added; fresh xanthine oxidase and catalase were added after 1 h; after completion of the reaction as determined by spectrophotometer, uric acid was precipitated by acidifying the solution with acetic acid to pH 4.6, washed twice with 0.05 M K-acetate pH 4.5, and dried for later use.

Protein Expression and Purification

A cDNA clone corresponding to the coding sequence of MuraH transcript variants lacking the PTS2 signal was PCR-amplified using a high-fidelity thermostable DNA polymerase (Deep Vent DNA polymerase, Biolabs) and two sequence specific primers: a NdeI-tailed upstream primer (5'-CATATGGCTACCGAGAGCAGTC-3') (SEQ ID NO: 5) and a BamHI-tailed downstream primer (5'-GGATCCCTT-TAACTCCCCCGG-3') (SEQ ID NO 6). The amplification product was inserted into the pNEB193 vector (Biolabs) to generate the intermediate vector pNEB-MuraII. The restriction fragment obtained from NdeI/BamHI digestion of plasmid pNEB-MuraH was then ligated into the dephosphorylated NdeI and BamHI sites of the expression vector pET11b (Novagen), and the resulting plasmid (pET-MuraH) was electroporated into *E.coli* BL21 (DE3) cells. The cloning of the cDNA sequence corresponding to the complete MuraD coding sequence was conducted the above-described method using a NdeI-tailed upstream primer (5'-CATATGGACATG-GTGAAGGTCAAT-3') (SEQ ID NO: 7) and a BamHI-tailed downstream primer (5'-GGATCCTCACGGTAGTTCCAC-3') (SEQ ID NO: 8). The expression of MuraH and MuraD were induced by adding 1 mM isopropyl-1-thio-β-D-galactopyranoside; after a 4 h incubation at 28° C., cells were lysed by twenty 30 second bursts of sonication. MuraH was purified using an anion exchange chromatography (Q Sepharose, Pharmacia Biotech), with a final yield of approximately 5 mg/liter of cell culture. MuraD was purified by using a gel filtration chromatography (Sephadex-G100, Pharmacia) obtaining a final yield of approximately 12 mg/liter.

Spectroscopy

Figure 2:
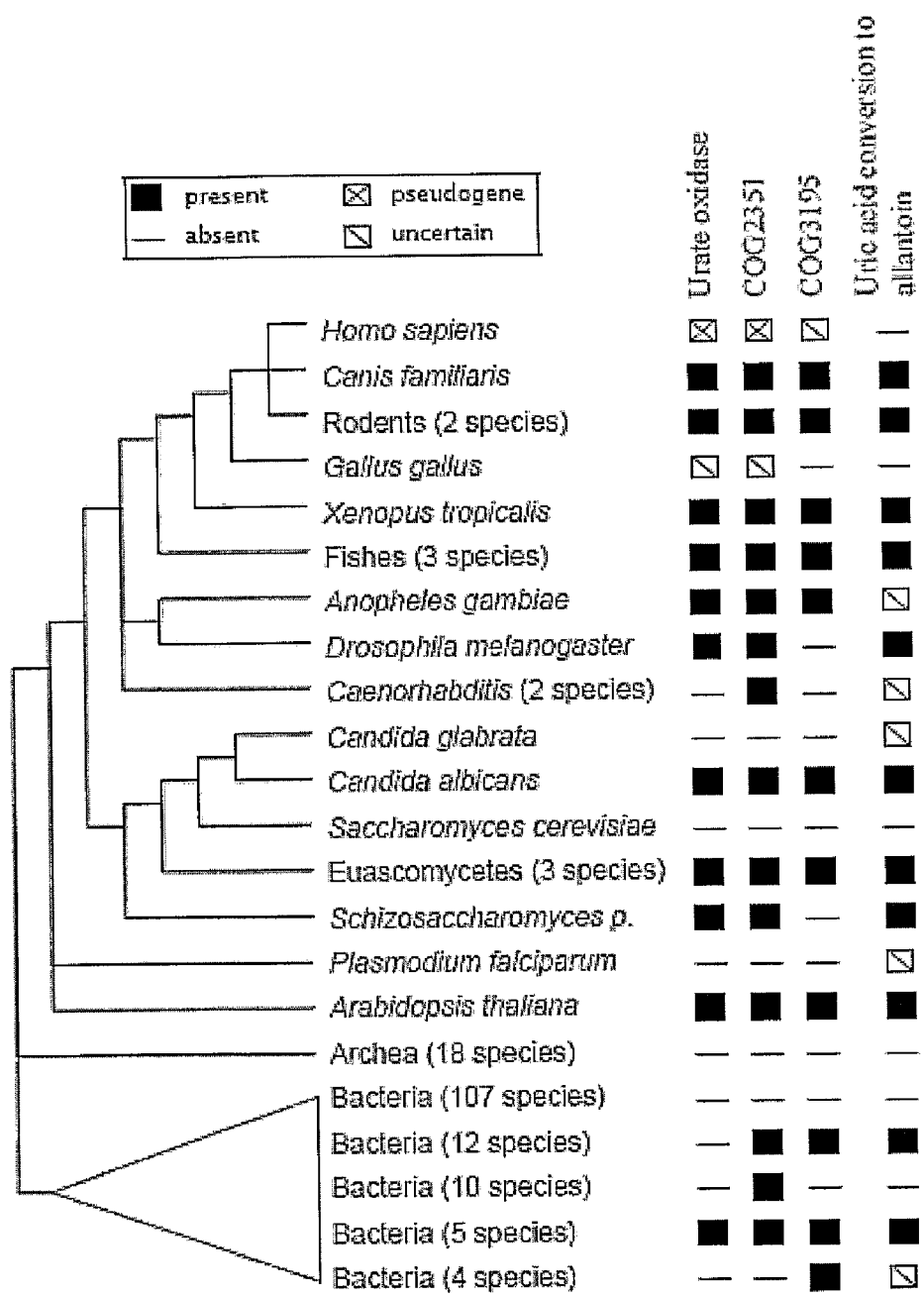
FIG. 2. Phylogenetic comparison of urate oxidase, HIU hydrolase (COG2351), OHCU decarboxylase (COG3195) in whole genomes. The pattern of presence and absence of urate oxidase, COG2351, and COG3195 is shown in a phylogenetic context and compared to the organisms ability to degrade uric acid. The tree represents the phylogeny of the species and is meant to infer the number of correlated events of gene loss/gain; phylogeny follows the NCBI taxonomy database; relationships among bacteria are not shown.

Spectrophotometric measures were conducted at 25° C. with a Varian Cary 1E spectrophotometer, using 1.68 µg of urate, 0.13 U of *Candida utilis* UO, 0.27 µg MuraH, in a 100 µL solution 0.1 M potassium phosphate pH 7.6. Circular dichroism (CD) measures were conducted at 25° C. with a Jasco J715 spectropolarimeter, using 16.8 µg of urate, 1.3 U of *Candida utilis* UO, 0.5 µg of MuraH, 1.26 µg of MuraD in a 1 mL solution 0.1 M potassium phosphate pH 7.6. The CD spectrum of HIU was obtained by data collected over the spectral range of 200-350 nm recorded after 20 seconds of urate oxidation with UO; the CD spectrum of OHCU was calculated by fitting time-course data to the two-step decay model (HIU→OHCU→X) (Kahn and Tipton, 1998, *Biochemistry*, 33, 11651-11659). Because the calculated spectrum was found to correspond to the OHCU spectrum observed in presence of HIU hydrolase after 40 seconds, the experimental spectrum was reported in the FIG. 2. Rate constants for the non-enzymatic decay of HIU and OHCU were obtained by fitting curves at 312 nm (HIU) and 257 nm (OHCU) to a single-exponential model; rate constants for the non-enzymatic formation and decay of OHCU were obtained by fitting curves at 257 nm to a model of exponential growth and decay. To obtain $^{13}C$ NMR spectra of urate, a 2 mM solution of [13C,15N]urate in 0.1 M potassium phosphate, pD 7.6 in 80% $D_2O$ was used. To obtain $^{13}C$ NMR spectra of the enzymatic conversion product, the solution was supplemented with 20 U of *Candida utilis* UO plus 20 U of catalase to remove hydrogen peroxide, 1.28 μg of HIU hydrolase, and 4.5 μg OHCU decarboxylase; the solution was gently shaken for 3 min and then transferred in a 5 mm NMR tube to acquire spectra at different times. The $^{13}$C NMR spectra were proton decupled and were collected at 17° C. with a VARIAN Inova 600 instrument.

Results

In order to find putative additional enzymes in the biological conversion of uric acid to allantoin, the authors sought proteins with a functional link to urate oxidase (UO), the first enzyme of the pathway. Functional links between different proteins can be inferred through genome comparisons, by the identification of a relationship among the corresponding genetic elements. Three criteria were used for this identification:

1) the authors examined genes of unknown function that are found in the neighbourhood of the gene coding for UO; the rationale for this criterion is that genes that have a coordinated expression, and hence a related function, tend to be physically clustered, as observed frequently but not exclusively in prokaryotic genomes (Snel et al., 2002, *Proc Natl Acad Sci USA*, 9, 5890-5895; Hurst et al., 2004, *Nat Rev Genet*, 4, 299-310).
2) the authors looked for cases in which UO is fused together with other proteins; such instances indicate that the two proteins can generally interact even when they are encoded by distinct polypeptide chains (Marcotte et al., 1999, *Science*, 5428, 751-753).
3) the authors selected genes that show a pattern of presence and absence across a range of genomes that is similar to that observed for UO; common 'phylogenetic profiles' (Pellegrini et al., 1999, *Proc Natl Acad Sci USA*, 8, 4285-4288) of different genes indicate that the different traits are under a common selective pressure and hence there is a functional relationship among them.

The authors used both a search based on visual inspection of genome sequences and annotations, and the database-screening program String (von Mering, Jensen et al., 2005, *Nucleic Acids Res*, Database issue, D433-437). Two COGs (Clusters of Orthologous Genes (Tatusov et al., 1997, *Science*, 5338, 631-637)), COG2351 and COG3195, of unknown function linked to UO according to the aforementioned criteria (Table 1) were found with the two methods.

are found in the neighbourhood of UO gene in five genomes. In two instances, genes of COG3195 appear to be fused with the gene coding for UO. Finally, the presence or absence of both COGs across different genomes parallels that observed for UO. A closer inspection at the various proteins of these families revealed that there were indications that a member of the COG2351 was involved in uric acid degradation, even tough this information was not propagated in database annotations. In fact, deletion mutants of the gene from *Bacillus subtilis*, named PucM, were found to be defective in UO activity (Schultz et al., 2001, *J Bacteriol,* 11, 3293-3302). Nevertheless, members of COG2351 have been subsequently studied in light of their similarity with the thyroid hormone transporter transthyretin (TTR); no binding activity for the known TTR ligands has been observed (Eneqvist et al., 2003, *Eur J Biochem*, 3, 518-532).

On the grounds of the evidence obtained by genome comparison, the authors devised experiments to investigate the role of the two protein families in uric acid metabolism. Mouse genes, designated as MuraH (COG2351) having the following nucleotide sequence (SEQ ID NO: 1):

```
ATGGCTACCGAGAGCAGTCCCCTGACTACTCACGTTCTAGACACTGCCTC

AGGGCTCCCTGCCCAAGGCCTCTGCCTCCGGCTGTCCCGCCTGGAGGCCC

CCTGCCAGCAGTGGATGGAGCTGAGGACAAGCTACACAAACCTGGACGGT

CGCTGTCCTGGGCTCCTGACACCAAGCCAGATAAAGCCAGGCACCTATAA

GCTGTTCTTCGACACAGAGCGCTACTGGAAAGAGCGGGGTCAAGAGAGCT

TTTACCCCTATGTAGAGGTGGTTTTCACTATTACAAAGGAGACCCAGAAG

TTCCACGTACCTCTGCTGCTGAGCCCATGGTCCTACACCACCTACCGGGG

GAGTTAA
``` and MuraD (COG3195) having the following nucleotide sequence (SEQ ID NO: 3):

```
ATGGACATGGTGAAGGTCAATTCCATGGACTTCGGAGAATTTGTGGATGT

GTTTGGGAACATTGTTGAGAAATGCCCTCTGATTGCCGCTGCTGTCTGGT
```

TABLE 1

Predicted functional association of urate oxidase (COG3648)

| COG | Description | Neighborhood | Gene fusion | Co-occurrence | Combined score |
|---|---|---|---|---|---|
| COG3195 | Uncharacterized protein conserved in Bacteria | 0.56 | 0.64 | — | 0.84 |
| COG2351 | Transthyretin-like protein | 0.64 | — | 0.13 | 0.68 |
| COG2233 | Xanthine/uracil permeases | 0.28 | — | — | 0.28 |

Output of the String program of a search conducted with the urate oxidase family; the reported scores correspond to the probability of finding the linked proteins within the same KEGG (Kyoto Encyclopedia of Genes and Genomes) pathway (von Mering, Jensen et al., 2005, *Nucleic Acids Res*, Database issue, D433-437).

COG2351 and COG3195 gene families appear even more correlated to UO than gene families that are known to be involved in urate degradation, among which the strongest correlation is found in the xanthine permease family (COG2233). Genes belonging to COG2351 and COG3195

-continued

```
CCCAGCGTCCATTCTCTGGCTTGGAAGACTTAGAAAATCACTTTTTTGCC

TTTATTGATGCTCTCCCGAGATCAGGCCAGGAAGGCATCCTGCGTTGTCA

CCCGGACCTAGCTGGCCGTGATCTGCAACAGGGCACACTCACTGCTGAGT

CACAGCGTGAGCAGAGCCAAGCAGGTCTCACTAGCCTAGACACCGACGAC

AGGCTGCGGCTGCAGCAACTCAATGCTCAGTACCGTGAGCGCTTCGGCTT

TCCGTTCGTTCTGGCAGCGCGCCTGAGCGACCGTGCCACTGTGCCCCGAG
```

```
AGCTAGCCCGCAGGCTTCAGTGCCAGCCGGAATCCGAGCTGCGCACCGCC

CTGGGTGAAGTGAAGAAGATCAGCCACCTGCGCCTGACAGATTTGCTCGG

TGCCCACTCCCACTCCGCCAGGGTGGAACTACCGTGA
``` were expressed in recombinant form and the corresponding proteins purified to near homogeneity.

The authors tested the activity of the two proteins on the conversion of 5-hydroxyisourate (HIU). The biochemical pathway leading to HIU is shown in the following scheme:

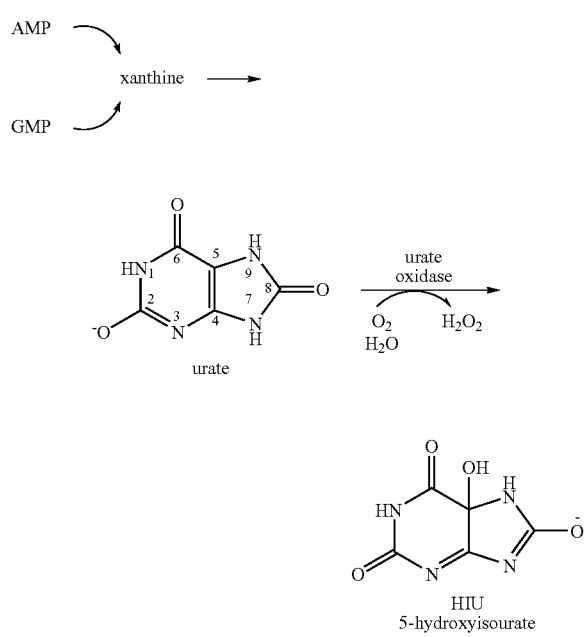

Degradation of purine nucleotides AMP and GMP converges to the nitrogen base xanthine; oxidation of xanthine yield uric acid (N3-deprotonated urate at neutral pH) (Kahn, Serfozo et al., 1997, *J. Am. Chem. Soc.*, 119, 5435-5442) that is further oxidised into HIU by the UO enzyme. HIU is a relatively unstable compound which undergoes spontaneous hydrolysis, as can be revealed by spectrophotometric analysis (Kahn and Tipton, 1998, *Biochemistry*, 33, 11651-11659). The reactions following HIU hydrolysis can not be easily monitored spectrophotometrically, as HIU and its decomposition products have overlapping absorbance in the UV region. However, since optically active compounds are produced, the reaction can be conveniently monitored by circular dichroism spectroscopy. The reactions that occur after urate oxidation are shown in the following scheme:

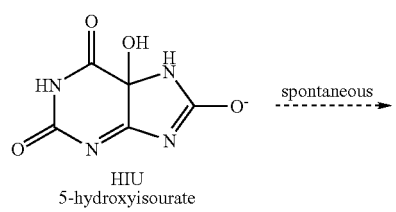

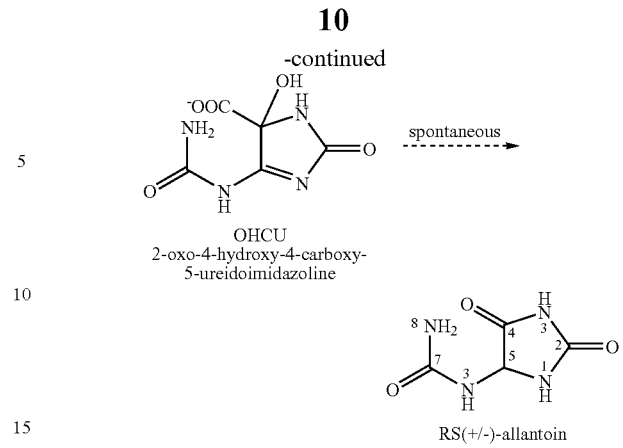

Levorotatory HIU, which is produced by the enzymatic oxidation of optically inactive urate, undergoes spontaneous hydrolysis; the hydrolysis of HIU between atoms N1 and C6 retains the configuration at the anomeric centre C5, and produces levorotatory 2-oxo-4-hydroxy-4-carboxy-5-ureidoimidazoline (OHCU) (Kahn and Tipton, 1998, *Biochemistry*, 33, 11651-11659); OHCU undergoes spontaneously decarboxylation to give optical inactive (racemic) allantoin as a stable end product (Modric, Derome et al., 1992, *Tetrahedron Letters*, 44, 6691-6694; Kahn, Serfozo et al., 1997, *J. Am. Chem. Soc.*, 119, 5435-5442).

Figure 3:
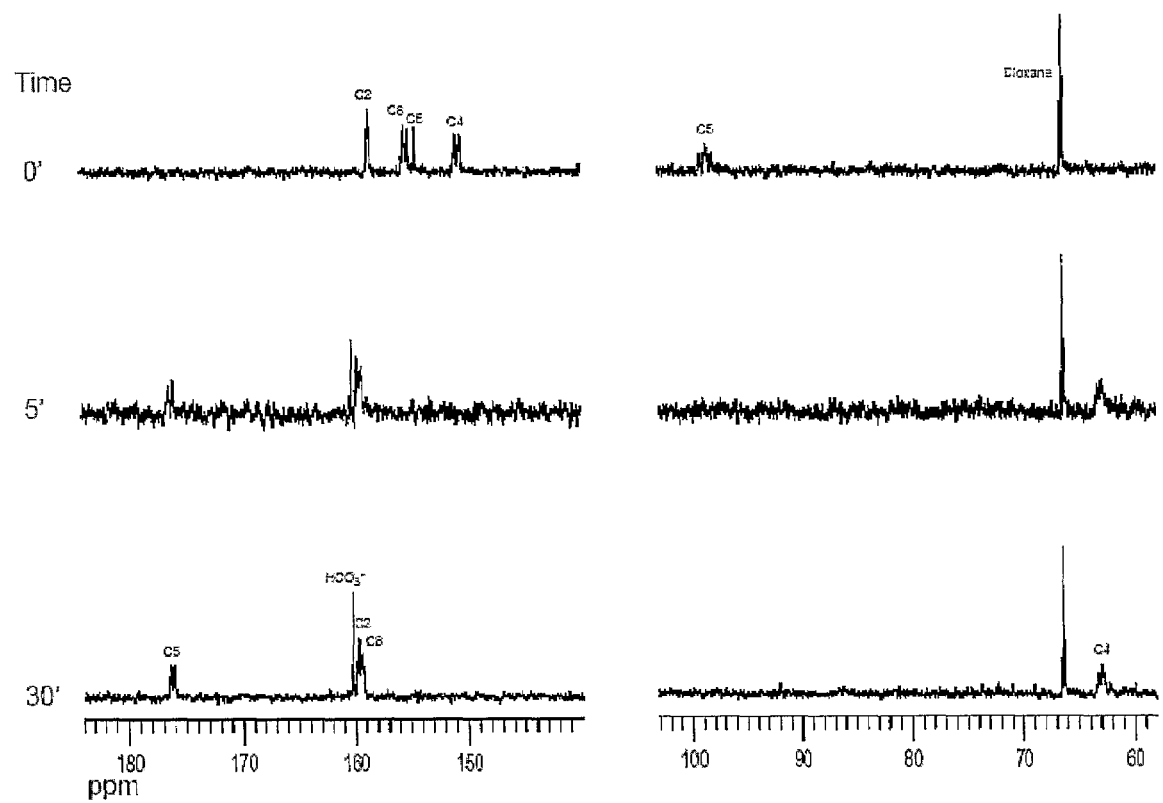
FIG. 3. $^{13}$C NMR of the conversion of [$^{15}$N,$^{13}$C]urate catalysed by UO, HIU hydrolase and OHCU decarboxylase; NMR spectra were collected at 17°, 0.1 M sodium phosphate, 80% D$_2$O, pD 7.6, in absence (Time 0') or presence (Time 5', 30') of UO, MuraH, MuraD. Carbon assignment is reported above peaks; atom numbering scheme is based on the urate carbon skeleton. Known chemical shifts for urate (Kahn, Serfozo et al., 1997, *J. Am. Chem. Soc.*, 119, 5435-5442) are: C2=158.8; C4=150.6; C5=98.8; C6=155.0; C8=155.6; Know chemical shift for allantoin (Kahn, Serfozo et al., 1997, *J. Am. Chem. Soc.*, 119, 5435-5442) are: C2=159.8; C4=63.2; C5=175.7; C8=159.0; HCO$_3^-$=160.3.

CD spectra of the optically active intermediates of uric acid conversion (FIG. 2a) show that, by observing signals at 312 nm (where only HIU has a strong ellipticity) and 257 nm (where only OHCU has a strong ellipticity), the two chemical species HIU and OHCU, respectively, can be selectively monitored in the course of the reaction. When urate conversion is performed in the presence of urate oxidase only (FIG. 2b), a rapid formation of HIU is observed, followed by spontaneous decay at a rate constant of $1.6 \cdot 10^{-3}$ $s^{-1}$; OHCU is produced at the same rate as HIU hydrolysis and decays at a rate constant of $1.2 \cdot 10^{-3}$ $s^{-1}$. When MuraH is added to urate conversion (FIG. 2c), a rapid decomposition of HIU and a concomitant formation of OHCU are observed, followed by a decay of OHCU at the same rate constant as in the uncatalysed reaction observed in FIG. 2b. Addition of MuraD to urate conversion (FIG. 2d) does not affect the decomposition rate of HIU, however no accumulation of OHCU is observed. When all enzymes (UO, MuraH and MuraD) are present in the reaction (FIG. 2e), the rapid formation of a stable, optically active product is observed. The product has been identified as allantoin by $^{13}C$ NMR spectroscopy (FIG. 3), exhibiting a CD spectrum corresponding to the mirror image of the known spectrum of R(−)-allantoin ('s-Gravemnade et al., 1969, *Recl. Trav. Chim. Pays-Bas*, 929-939). The authors therefore conclude that the reaction product obtained is S—(+)-allantoin.

These results demonstrate that: 1) MuraH catalyses the conversion of HIU to the same product (OHCU) that is observed after spontaneous hydrolysis of HIU. Therefore, MuraH has HIU hydrolase activity; 2) MuraD catalyses the conversion of the product of HIU hydrolysis (OHCU) into S(+)-allantoin. Therefore, MuraD has OHCU decarboxylase activity. According to these data, the authors propose the following scheme for the degradation of uric acid into S(+)-allantoin (the so-called second step of the purine degradation pathway):

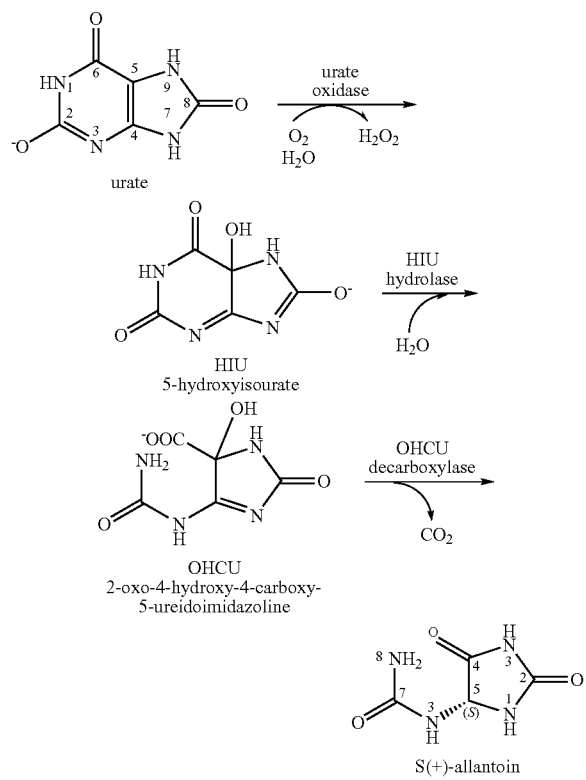

Urate is converted by urate oxidase into levorotatory HIU; hydrolysis of levorotatory HIU, catalysed by the enzyme HIU hydrolase (MuraH), gives levorotatory OHCU; its decarboxylation, catalysed by the enzyme OHCU decarboxylase (MuraD), gives dextrorotatory S(+)-allantoin.

Compared to the non-enzymatic decomposition of the products of urate oxidase, as characterised by Khan and Tipton (Kahn, Serfozo et al., 1997, J. Am. Chem. Soc., 119, 5435-5442; Kahn and Tipton, 1998, Biochemistry, 33, 11651-11659) and presented in schema 2, the enzymatic reaction described in the present invention represents a shorter but not divergent pathway. In fact, the chemical species of the reaction catalyzed by HIU hydrolase and OHCU decarboxylase are also formed spontaneously after urate oxidation. In spite of this, phylogenetic comparison of whole genomes (FIG. 2) shows that gene encoding these enzymes are selectively required in organisms that are known to convert uric acid to allantoin. The patterns of presence and absence of these genes is very peculiar when compared to species phylogeny. Urate oxidase has been gained or lost several time during species evolution; these events have been accompanied by a parallel gain/loss of HIU hydrolase (COG2351) and OHCU decarboxylase (COG3195). At least seven independent instances of correlated events are counted in the shown phylogenetic tree (more if a resolved bacterial phylogeny is taken into account). Analysis of across-species correlation thus provides evidence that the functional link between urate oxidase and the two other gene families has been maintained during the evolution from bacteria to mammals. This does indeed imply that ortholog genes of MuraH and MuraD (namely genes belonging to COG2351 and COG319) are expected to encode proteins having the catalytic function of MuraH and MuraD, being then ortholog encoded variants thereof.

Figure 4:
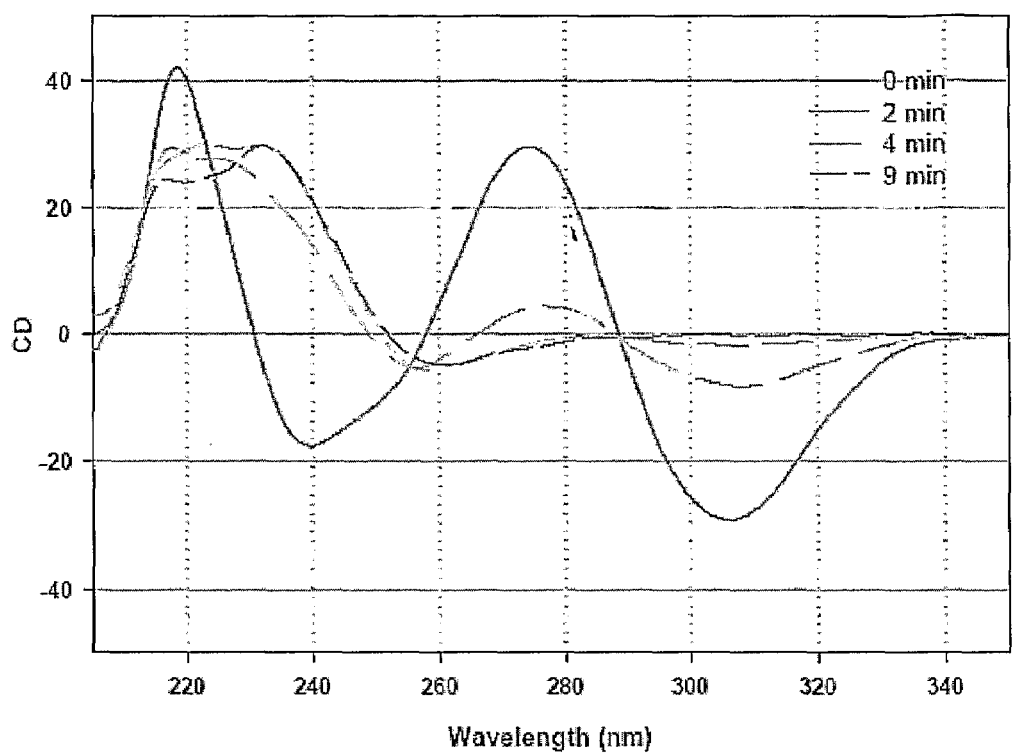
FIG. 4. Time-resolved CD spectra of the urate oxidase reaction in presence of borate ions (0.05 M Tris-HCl pH 8 supplied with 0.01 M borate buffer). a) Time course of urate oxidation with UO. b) Time course of the urate oxidation with UO+MuraH+MuraD.
Figure 4:
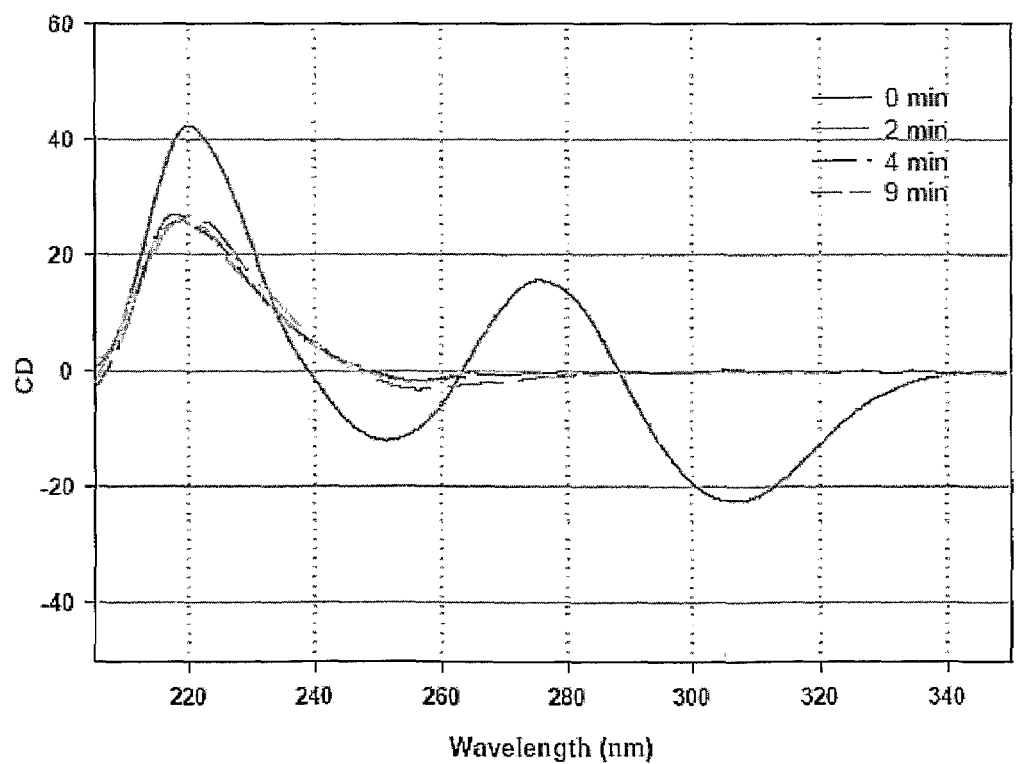

Given that allantoin can be produced in vitro by the sole action of urate oxidase, one may wonder why the selective pressure for the maintenance of HIU hydrolase and OHCU decarboxylase is so strong that not a single case is observed in nature in which only urate oxidase is used for uric acid degradation. One reason may be related to the efficiency of the reaction, both in terms of rate and stereochemistry. Indeed, spontaneous decay of urate oxidation products is rather slow and produces (+/−)-allantoin, while the subsequent enzyme of the pathway, allantoinase, is generally stereospecific for the dextrorotatory form (Mulrooney and Hausinger, 2003, J Bacteriol, 1, 126-134). Another, perhaps more important reason may be the need to limit lifetime of reactive chemical species. Allantoin is a rather inert compound, whereas the intermediates of the reaction are particularly prone to further oxidation to yield undesirable products (Santos, Anjos et al., 1999, Arch Biochem Biophys, 2, 285-294), and it is well known that oxidation of uric acid can yield different end products depending on the reaction conditions (Priest and Pitts, 1972, Anal Biochem, 1, 195-205). By contrast, the output of the full enzymatic pathway is less subjected to reaction environment. Dextrorotatory allantoin, for example, is still produced in presence of 0.01 M borate ions (FIG. 4), a condition in which the non enzymatic spontaneous decay of the intermediates yields alloxanate (Priest and Pitts, 1972, Anal Biochem, 1, 195-205).

Figure 5:
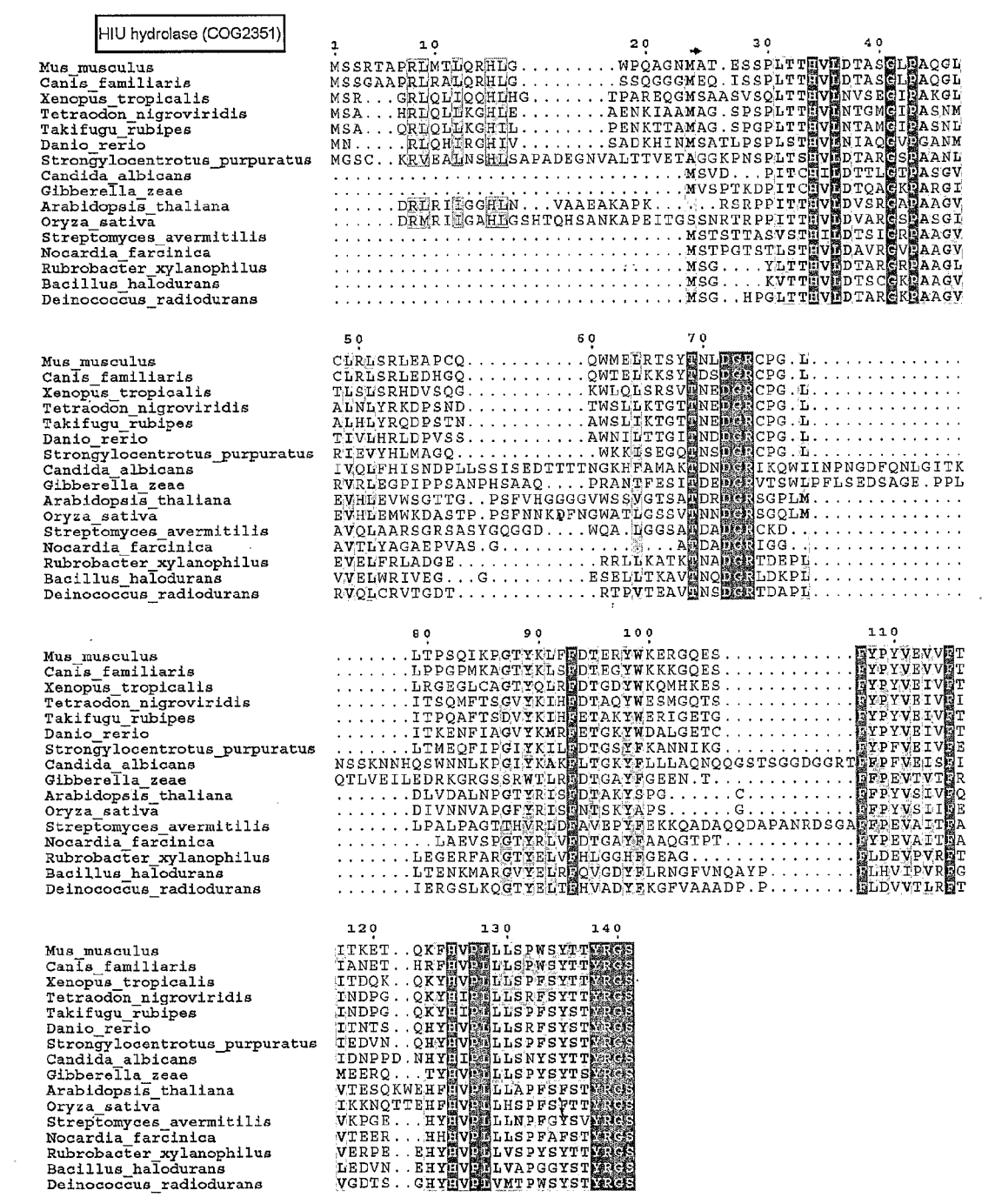
Figure 6:
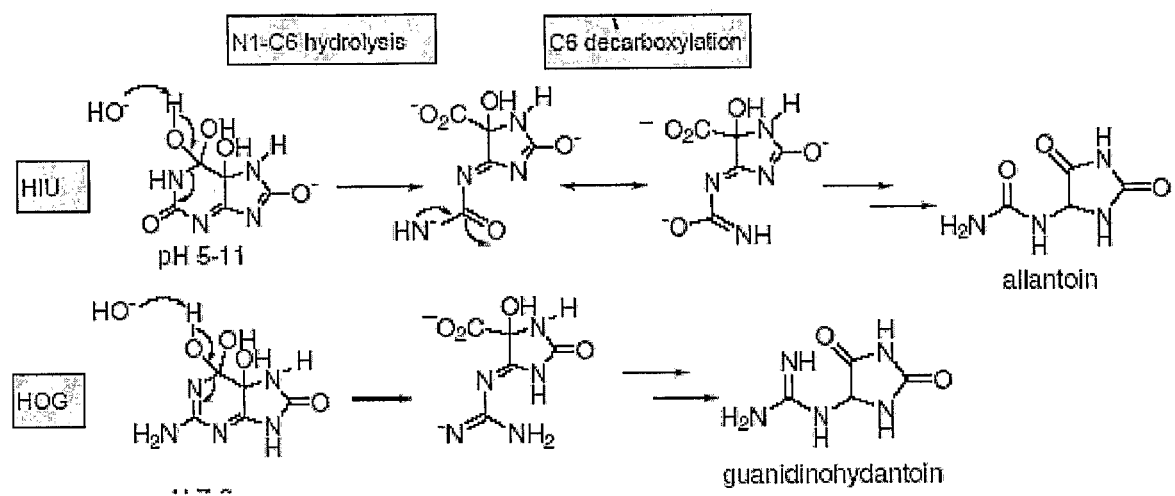
FIG. 6 Scheme of the degradation pathway of 5-hydroxyisourate (HIU) and of 5-hydroxy-8-oxo-7,8-dihydroguanine (HOG). The scheme is drawn to highlight the similarity between HIU and HOG, and the similarity between their degradation pathway which involves N1-C6 hydrolysis and C6 decarboxylation.

Comparison of HIU hydrolase and OCHU decarboxylase sequences in various organisms illustrate some aspects of the evolution and function of these enzymes. HIU hydrolases (FIG. 5) are proteins of about 120 amino acids that can fold in a multimeric structure (the MuraH monomer has Mw of 13.559 whereas a Mw of about 50,000 was estimated for the native protein). The amino acid sequence has a clear similarity with transthyretin from which HIU hydrolase can be readily distinct by a conserved carboxy-terminal tetrapeptide—YRGS—(SEQ ID NO: 38) that is a signature of the family (Eneqvist, Lundberg et al., 2003, Eur J Biochem, 3, 518-532). Metazoan sequences have a previously unnoticed N-terminal extension of about 20 amino acids encoded by a short exon absent in other organisms. This part of the protein has a conserved nonapeptide whose consensus pattern, RLx2Ix2HL (SEQ ID NO: 39), corresponds to the peroxisornal targeting signal 2 (PTS2) (Swinkels et al., 1991, Embo J, 11, 3255-3262). Presence of this kind of signal is not surprising given that UO activity resides in peroxisomes. Interestingly, the analysis of mouse Expressed Sequence Tags shows that the same gene also produces alternative transcripts in which the translation initiation codon is a conserved methionine in the second exon. In this latter case, the encoded protein lacks the peroxisome targeting signal and, therefore, will likely have a different cellular localisation. A dual localisation of HIU hydrolase is not inconsistent with a unique activity in uric acid metabolism, since proteins of the purine degradation pathway are frequently found in different cellular compartment (Hayashi et al., 2000, Cell Biochem Biophys, 123-129). However, this can also suggest possible additional functions. In this regard, it is worth recalling the already noticed striking similarity between 5-hydroxyisourate and modified purines that originate from oxidative DNA damage (Yu et al., 2004, Org Lett, 19, 3417-20). For example, the modified purine hydroxy-8-oxo-7,8-dihydroguanine has a structure analogous to 5-hydroxyisourate and its postulated degradation pathway involves the same reactions that are catalysed by HIU hydrolase and OHCU decarboxylase (FIG. 6).

Contrary to HIU hydrolase, the OHCU decarboxylase family (FIG. 7) has no apparent similarity with other proteins. OHCU decarboxylases are proteins of about 180 amino acids that, alike HIU hydrolases, can fold in a multimeric structure (the MuraD monomer has a Mw of 20.016 whereas a Mw of about 50,000 was estimated for the native protein). A recognizable carboxy-terminal peroxisomal targeting signal (PTS1) (Gould et al., 1987, J Cell Biol, 6 Pt 2, 2923-2931) is present in most eukaryotic sequences but absent in plants. Reinforcing the biochemical link between OHCU decarboxylase and HIU hydrolase, plants have the two proteins fused in a single polypeptide chain with a OHCU decarboxylase sequence at the N-terminus and a HIU hydrolase sequence at the C-terminus. The bifunctional form is ubiquitous in seed plants. Soybean, however, also possess a different enzyme, related by homology to glycosidases, able to catalyse hydrolysis of HIU to OHCU (Sarma, Serfozo et al., 1999, *J Biol Chem*, 48, 33863-33865). This peculiarity is not surprising for leguminous plants which have a complex purine metabolism and use compounds deriving from urate oxidation for nitrogen storage and transport. HIU hydrolase and OHCU decarboxylase are encoded by two ancient families of orthologous genes that are expected to function in purine metabolism in a variety of organisms, from bacteria to mammals. Humans, which are unable to degrade uric acid, are an important exception. In humans, the HIU hydrolase gene has several inactivating mutations, and the OHCU decarboxylase gene, though potentially coding for a complete protein, do not appear to be expressed, as can be judged by transcriptome data. These two proteins have, nevertheless, important implications for our species. In regard to human evolution, it is known that hominoids have lost their capacity to metabolize uric acid because of the inactivation of the UO gene occurred in a primate ancestor about 15 million years ago (Oda, Satta et al., 2002, *Mol Biol Evol*, 5, 640-653). The subsequent inactivation of the genes coding for the other enzymes of the pathway is a likely, though not unique, evolutionary scenario.

Several diseases such as gout, stones, renal failure are known to be associated with abnormally high levels of uric acid in blood serum (hyperuricemia) (Hall et al., 1967, *Am J Med*, 1, 27-37). An elective treatment for acute manifestations of hyperuricemia—particularly for the burst of uric acid that characterises the tumor lysis syndrome—is the administration of urate oxidase (Bomalaski and Clark, 2004, *Curr Rheumatol Rep*, 3, 240-247). However, the chemical intermediates produced by urate oxidation can be reactive molecules leading to undesirable side reactions.

In the present invention, the authors show that urate oxidase is not the unique enzyme involved in uric acid degradation. Indeed two novel enzymes, MuraH and MuraD, are shown to possess HIU hydrolase and OHCU decarboxylase activity leading to the conversion of uric acid into S(+)-allantoin. The use of these two enzymes could greatly improve the treatment of hyperuricemia.

BIBLIOGRAPHY

Ames, B. N., R. Cathcart, E. Schwiers and P. Hochstein (1981). *Proc Natl Acad Sci USA* 78(11): 6858.
Barker, D. and M. Pagel (2005). *PLoS Comput Biol* 1(1): e3.
Bomalaski, J. S. and M. A. Clark (2004). *Curr Rheumatol Rep* 6(3): 240-247.
Bongaerts, G. P. and G. D. Vogels (1979). *Biochim Biophys Acta* 567(2): 295-308.
Eneqvist, T., E. Lundberg, L. Nilsson, R. Abagyan and A. E. Sauer-Eriksson (2003). *Eur J Biochem* 270(3): 518-532.
Gouet, P., E. Courcelle, D. I. Stuart and F. Metoz (1999). *Bioinformatics* 15(4): 305-308.
Gould, S. G., G. A. Keller and S. Subramani (1987). *J Cell Biol* 105(6 Pt 2): 2923-2931.
Hall, A. P., P. E. Barry, T. R. Dawber and P. M. McNamara (1967). *Am J Med* 42(1): 27-37.
Hayashi, S., S. Fujiwara and T. Noguchi (2000). *Cell Biochem Biophys* 32 Spring: 123-129.
Hurst, L. D., C. Pal and M. J. Lercher (2004). *Nat Rev Genet* 5(4): 299-310.
Kahn, K., P. Serfozo and P. A. Tipton (1997) *J. Am. Chem. Soc.* (119): 5435-5442.
Kahn, K. and P. A. Tipton (1998). *Biochemistry* 37(33): 11651-11659.
Lee, Y., H. Lee do, C. W. Kho, A. Y. Lee, M. Jang, S. Cho, C. H. Lee, J. S. Lee, P. K. Myung, B. C. Park and S. G. Park (2005). *FEBS Lett* 579(21): 4769-4774.
Locatelli, F. and F. Rossi (2005). *Contrib Nephrol* 147: 61-8.
Marcotte, E. M., M. Pellegrini, H. L. Ng, D. W. Rice, T. O. Yeates and D. Eisenberg (1999). *Science* 285(5428): 751-753.
Modric, N., A. E. Derome, S. J. H. Ashcroft and Poje, M. (1992). *Tetrahedron Letters* 33(44): 6691-6694.
Mulrooney, S. B. and R. P. Hausinger (2003). *J Bacteriol* 185(1): 126-134.
Oda, M., Y. Satta, O. Takenaka and N. Takahata (2002). *Mol Biol Evol* 19(5): 640-653.
Pea, F. (2005). *Contrib Nephrol* 147: 35-46.
Pellegrini, M., E. M. Marcotte, M. J. Thompson, D. Eisenberg and T. O. Yeates (1999). *Proc Natl Acad Sci USA* 96(8): 4285-4288.
Priest, D. G. and O. M. Pitts (1972) *Anal Biochem* 50(1): 195-205.
Santos, C. X., E. I. Anjos and O. Augusto (1999). *Arch Biochem Biophys* 372(2): 285-294.
Sarma, A. D., P. Serfozo, K. Kahn and P. A. Tipton (1999). *J Biol Chem* 274(48): 33863-33865.
Schlesinger, N. (2004). *Drugs* 64(21): 2399-416.
Schultz, A. C., P. Nygaard and H. H. Saxild (2001). *J Bacteriol* 183(11): 3293-3302.
's-Gravenmade, E. J., G. D. Vogels and C. van Pelt (1969). *Recl. Trav. Chim. Pays-Bas* 88: 929-939.
Snel, B., P. Bork and M. A. Huynen (2002). *Proc Natl Acad Sci USA* 99(9): 5890-5895.
Stryer, L. (1995). *Biochemistry*. New York, W.H. Freeman.
Swinkels, B. W., S. J. Gould, A. G. Bodnar, R. A. Rachubinski and S. Subramani (1991). *Embo J* 10(11): 3255-3262.
Tatusov, R. L., E. V. Koonin and D. J. Lipman 1997). *Science* 278(5338): 631-637.
Vogels, G. D. and C. Van der Drift (1976). *Bacteriol Rev* 40(2): 403-468.
von Mering, C., L. J. Jensen, B. Snel, S. D. Hooper, M. Krupp, M. Foglierini, N. Jouffre, M. A. Huynen and P. Bork (2005). *Nucleic Acids Res* 33 (Database issue): D433-437.
Wortmann, R. L. (2002). *Curr Opin Rheumatol* 14(3): 281-6.
Yu, H., J. C. Niles, J. S. Wishnok and S. R. Tannenbaum (2004). *Org Lett* 6(19): 3417-20.

The invention claimed is:

1. An isolated polypeptide molecule able to selectively modulate conversion of uric acid oxidation products into S(+)-allantoin comprising the amino acid sequence of SEQ ID NO: 4.

2. A composition comprising the polypeptide of claim 1 together with appropriate excipients.

3. The composition according to claim 2 further comprising a polypeptide of SEQ ID NO: 2, together with appropriate excipients.

4. The composition according to claim 2 further comprising a pharmacologically active amount of urate oxidase.

5. A process to selectively modulate uric acid conversion into S allantoin comprising a step of incubating uric acid under appropriate conditions with the polypeptide of claim 1 and urate oxidase.

* * * * *